United States Patent
Marik et al.

(10) Patent No.: US 12,214,058 B2
(45) Date of Patent: *Feb. 4, 2025

(54) IMAGING METHODS USING DEUTERATED COMPOUNDS

(71) Applicant: Genentech, Inc., South San Francisco, CA (US)

(72) Inventors: Jan Marik, Hillsborough, CA (US); Joseph P. Lyssikatos, Piedmont, CA (US); Simon Peter Williams, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 203 days.

This patent is subject to a terminal disclaimer.

(21) Appl. No.: 18/056,856

(22) Filed: Nov. 18, 2022

(65) Prior Publication Data

US 2023/0218782 A1 Jul. 13, 2023

Related U.S. Application Data

(63) Continuation of application No. 16/895,352, filed on Jun. 8, 2020, now Pat. No. 11,504,440, which is a continuation of application No. 16/050,453, filed on Jul. 31, 2018, now Pat. No. 10,675,367, which is a continuation of application No. 15/006,997, filed on Jan. 26, 2016, now Pat. No. 10,076,581, which is a continuation of application No. PCT/EP2015/060447, filed on May 12, 2015.

(60) Provisional application No. 61/992,717, filed on May 13, 2014.

(51) Int. Cl.
*A61K 51/04* (2006.01)
*C07B 59/00* (2006.01)
*C07D 487/04* (2006.01)

(52) U.S. Cl.
CPC ........ *A61K 51/0459* (2013.01); *C07B 59/002* (2013.01); *C07D 487/04* (2013.01); *C07B 2200/05* (2013.01)

(58) Field of Classification Search
CPC ....... A61K 51/00; C07D 513/04; C07B 59/00
See application file for complete search history.

(56) References Cited

U.S. PATENT DOCUMENTS

| | | |
|---|---|---|
| 8,318,132 B2 | 11/2012 | Kolb et al. |
| 8,491,869 B2 | 7/2013 | Gangadharmath et al. |
| 8,691,187 B2 | 4/2014 | Szardenings et al. |
| 10,076,581 B2 * | 9/2018 | Marik ............ A61P 25/00 |
| 10,675,367 B2 | 6/2020 | Marik et al. |
| 2009/0143432 A1 | 6/2009 | Jones et al. |
| 2010/0144657 A1 | 6/2010 | Gant et al. |
| 2010/0239496 A1 | 9/2010 | Gangadharmath et al. |
| 2011/0182812 A1 * | 7/2011 | Szardenings ........ C07D 487/04 424/9.1 |
| 2012/0302755 A1 | 11/2012 | Szardenings et al. |
| 2013/0302248 A1 | 11/2013 | Gangadharmath et al. |

FOREIGN PATENT DOCUMENTS

| | | |
|---|---|---|
| CN | 101522624 A | 9/2009 |
| DE | 76515 A1 | 10/1970 |
| EP | 2450332 A1 | 5/2012 |
| JP | 2013-522365 A | 6/2013 |
| WO | 03/072580 A1 | 9/2003 |
| WO | 2004/033451 A1 | 4/2004 |
| WO | 2007/126733 A1 | 11/2007 |
| WO | 2010/111303 A2 | 9/2010 |
| WO | 2011/119565 A1 | 9/2011 |
| WO | 2012/052409 A1 | 4/2012 |
| WO | 2012/065963 A2 | 5/2012 |
| WO | 2013/176698 A1 | 11/2013 |
| WO | 2015/052105 A1 | 4/2015 |

OTHER PUBLICATIONS

Ariza, M., et al., "Tau Positron Emission Tomography (PET) Imaging: Past, Present, and Future" ACS J Med Chem 58(11):4365-4382 (Feb. 11, 2015).
Belikov, Pharmaceutical Chemistry Moscow::pp. 27-29 (2007).
Buteau, K., "Deuterated Drugs: Unexpectedly Nonobvious" J High Tech Law 10(1):22-74 (2009).
Challapalli, A., et al., "Biodistribution and radiation dosimetry of deuterium-substituted 18F-fluoromethyl-[1, 2-2H4]choline in healthy volunteers" J Nucl Med 55(2):256-263 (Feb. 1, 2014).
Chien, D., et al., "Early clinical PET imaging results with the novel PHF-tau radioligand [F18]-T808" J Alzheimers Dis 38(1):171-184 (Oct. 29, 2013).
Dorokhov et al., "Synthesis of derivatives of the new heterocyclic system pyrimido[4',5':4,5]pyrimido [1,2-a]benzimidazole" Bulletin of the Academy of Sciences of the USSR, Division of chemical science 40(11):2262-2266 (Nov. 1991) http://rd.springer.com/content/pdf/10.1007/BF00961049.pdf.

(Continued)

*Primary Examiner* — Michael G. Hartley
*Assistant Examiner* — Jagadishwar R Samala
(74) *Attorney, Agent, or Firm* — Vasily Ignatenko

(57) ABSTRACT

The present invention relates to deuterated and optionally detectably labeled compounds of formula (I) and formula (V):

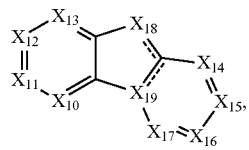

and salts thereof, wherein $R^1$, $R^2$, A, and $X_{10}$-$X_{19}$ have any of the values defined in the specification. Also included are pharmaceutical compositions comprising such compounds and salts, and methods of using such compounds and salts as imaging agents.

6 Claims, 12 Drawing Sheets

(56) References Cited

OTHER PUBLICATIONS

Gant, T.G.,, "Using Deuterium in Drug Discovery: Leaving the Label in the Drug" ACS J Med Chem 57(9):3595-3611 (Dec. 2, 2013).

Gao, M. et al., "Concise and high-yield synthesis of T808 and T808P for radiosynthesis of [(18)F]-T808, a PET tau tracer for Alzheimer's disease" Bioorg Med Chem Lett 24(1):254-257 (Jan. 1, 2014).

Jahan, M. et al., "Decreased defluorination using the novel beta-cell imaging agent [18F]FE-DTBZ-d4 in pigs examined by PET" EJNMMI Res 1(1):Article 33 (1-13) (Dec. 5, 2011).

Jensen, J., et al., "Research towards tau imaging" J Alzheimers Dis 26( Suppl 3):147-157 (Oct. 4, 2011).

Jiang, W., et al., "Application of deuteration in drug research" Qilu Pharma Affairs (w/Eng. Transl.), 29(11):682-684 (Dec. 31, 2010).

Mathis, C., et al., "Imaging tau deposits in vivo: progress in viewing more of the proteopathy picture" Neuron 79(6):1035-1037 (Sep. 18, 2013).

Matsumura, K., et al., "Synthesis and biological evaluation of novel styryl benzimidazole derivatives as probes for imaging of neurofibrillary tangles in Alzheimer's disease" Bioorg Med Chem 21(11):3356-3362 (Jun. 1, 2013).

Mohamed, M.A., et al., "Synthesis of some new of thieno[2,3-b]pyridines, pyrazolo[1,5-a]pyrimidine, [1,2,4]triazolo[1,5-a]pyrimidine, pyrazolo[5,1-c]triazine and pyrimido[1,2-a]benzimidazole derivatives containing pyridine moiety" Eur J Chem 2(4):509-513 (Dec. 31, 2011).

Nag, S., et al., "Development of a novel fluorine-18 labeled deuterated fluororasagiline ([(18)F]fluororasagiline-D2) radioligand for PET studies of monoamino oxidase B (MAO-B)" Bioorg Med Chem 21(21):6634-6641 (Nov. 1, 2013).

Schou, M., et al., "PET evaluation of novel radiofluorinated reboxetine analogs as norepinephrine transporter probes in the monkey brain" Synapse 53(2):57-67 (Aug. 1, 2004).

Timmins, G., "Deuterated drugs: where are we now?" Expert Opin Ther Pat 24(10):1067-1075 (Jul. 29, 2014).

Tipre, D., et al., "PET imaging of brain 5-HT1A receptors in rat in vivo with 18F-FCWAY and improvement by successful inhibition of radioligand defluorination with miconazole" J Nucl Med 47(2):345-353 (Feb. 1, 2006).

Witney, T., et al., "Evaluation of Deuterated 18F- and 11C-Labeled Choline Analogs for Cancer Detection by Positron Emission Tomography" Clin Cancer Res 18(4):1063-1072 (Feb. 15, 2012).

Xia, C., et al., "[18F]T807, a novel tau positron emission tomography imaging agent for Alzheimer's disease" Alzheimers Dement 9(6):666-676 (Nov. 1, 2013).

Zhang, W., et al., "A Highly Selective and Specific PET Tracer for Imaging of Tau Pathologies" J Alzheimers Dis 31(3):601-612 (Apr. 26, 2012).

\* cited by examiner

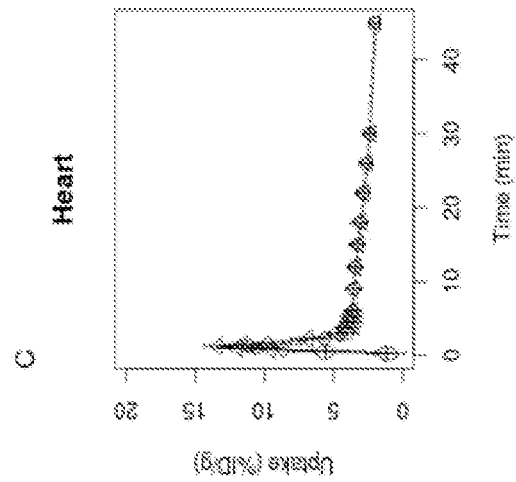
Figure 4A, Figure 4B, Figure 4C
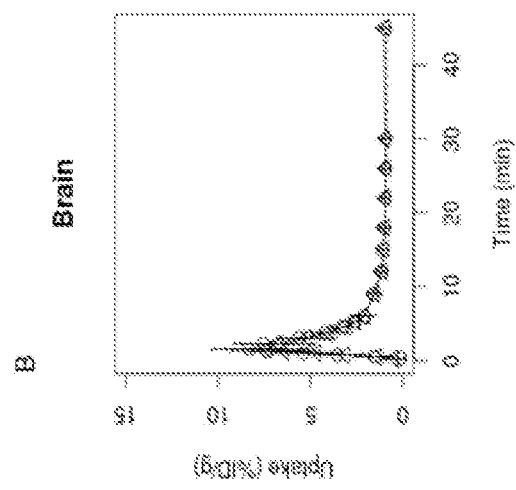
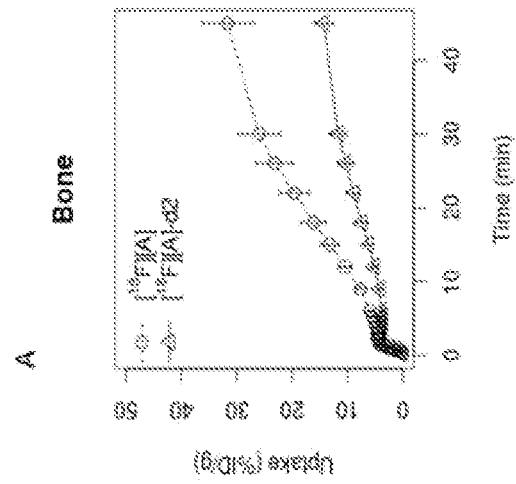

IMAGING METHODS USING DEUTERATED COMPOUNDS

CROSS-REFERENCE TO RELATED APPLICATIONS

This application is a continuation of U.S. application Ser. No. 16/895,352, filed Jun. 8, 2020, allowed, which is a continuation of U.S. application Ser. No. 16/050,453, filed Jul. 31, 2018, now U.S. Pat. No. 10,675,367, issued Jun. 9, 2020, which is a continuation of U.S. application Ser. No. 15/006,997, filed Jan. 26, 2016, now U.S. Pat. No. 10,076,581 issued Sep. 18, 2018, which is a continuation of International Application No. PCT/EP2015/060447, filed May 12, 2015, which claims the benefit of priority of U.S. Provisional Application No. 61/992,717, filed May 13, 2014, the contents of each of which are incorporated by reference in their entirety.

BACKGROUND OF THE INVENTION

Neurofibrillary tangles (NFTs) deposits are a hallmark of a variety of neuropathologies such as Alzheimer's disease (AD), progressive supranuclear palsy, frontotemporal dementia and parkinsonism linked to chromosome 17, Pick's disease, and dementia pugilistica. NFT plaques are comprised of aggregated hyperphosphorylated tau protein. Tau is a protein associated with cytoskeleton and involved in the transport of vesicles along microtubules in neurons. Under pathological conditions, tau is hyperphosphorylated and forms beta-sheet aggregates with fibrillar appearances similar to Aβ in senile plaques. Some tau-targeted therapies aim to slow disease progression by interfering with cell-to-cell transfer of soluble tau oligomers capable infecting adjacent cells by a prion mechanism. Alternatively, tau-targeted therapies aim to inhibit tau oligomerization and/or aggregation to larger fibrils and tangles (Bulic, B., et al., *J Med. Chem.*, 2013 56 (11), 4135-55). Such strategies warrant reliable non-invasive tau-specific biomarkers for monitoring of current tau burden and disease progression. Tau-specific PET imaging biomarkers have the potential to non-invasively monitor disease progression and also provide a direct readout of tau-targeted agent efficacy and confirmation of its mechanism of action in clinical trials (Mathis, C. A.; Klunk, W. E., *Neuron* 2013 79 (6), 1035-7; and Jensen, J. R., et al., *J. Alzheimer's Disease:JAD* 2011 26 Suppl 3, 147-57).

Several tau-selective molecules were recently discovered and radiolabeled with positron emitting radionuclides for PET imaging. One of them, [$^{18}$F][A] was reported to bind tau aggregates in AD patient tissues with 22 nM affinity and demonstrated 27-fold selectivity for tau over Aβ amyloid which forms similarly structured fibrils. Initial clinical evaluation of [A] demonstrated its ability to clearly differentiate between AD patients and age matched controls. Moreover, the PET tracer distribution in patients with increasing MMSE score resembled tau localization described by the Braak score (Braak, H., et al., *Acta Neuropathol* 2006 112 (4), 389-404) found postmortem in tissues of patients with corresponding AD severity. Unfortunately, the oxidative metabolism of [A] led to dissociation of $^{18}$F from the molecule and accumulation of $^{18}$F fluoride in mineral bone. The undesired skull uptake can potentially interfere with quantification of cortical uptake of the tracer. See Xia, C. F., et al., *Alzheimer's Dement.* 2013 9 (6), 666-76; Zhang, W., et al., *J. Alzheimer's Disease:JAD* 2012 31 (3), 601-12; Chien, D. T., et al., *J. Alzheimer's Disease: JAD* 2013 34 (2), 457-68; and Chien, D. T., et al., *J. Alzheimer's Disease:JAD* 2014 38 (1), 171-84.

Currently there is a need for additional detectable compounds that bind to tau. In particular, there is a need for detectable compounds with improved in vivo properties, such as improved metabolism characteristics.

SUMMARY OF THE INVENTION

In one aspect the invention includes a deuterated detectable compound, or salt thereof, that binds to a tau protein.

Another aspect includes a compound of formula (I) or formula (V):

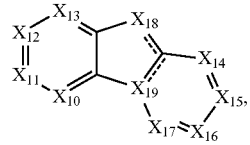

or a salt thereof, wherein:
$R^1$ is phenyl, naphthyl, 6-membered heteroaryl, 9- or 10-membered bicyclic heterocyclyl, 12-13 membered tricyclic carbocyclyl, or 12-13 membered tricyclic heterocyclyl, wherein $R^1$ is optionally substituted with one or more groups $R^a$, wherein $R^1$ is attached to the remainder of the compound of formula (I) at any synthetically feasible position;
A is absent, $C_{1-4}$alkylene, $C_{3-6}$cycloalkylene, $C_{2-4}$alkenylene, or $C_{2-4}$alkynylene;
$R^2$ is 6-, 9-, or 10-membered carbocyclyl or a 5-, 6-, 9-, or 10-membered heterocyclyl, which carbocyclyl and heterocyclyl is optionally substituted with one or more groups $R^b$, wherein $R^2$ is attached to the remainder of the compound of formula (I) at any synthetically feasible position;
each $X_{10}$-$X_{17}$ is independently CH or N;
$X_{18}$ is CH, N, O, or S; and
$X_{19}$ is CH, C, or N;
each ---- is independently absent or forms a double bond, provided only one ---- forms a double bond;
each $R^a$ is independently selected from oxo, $C_{1-6}$alkyl, $C_{2-6}$alkenyl, $C_{2-6}$alkynyl, —(O—CH$_2$—CH$_2$)$_m$—R$^c$, carbocyclyl, heterocyclyl, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any $C_{1-6}$alkyl, $C_{2-6}$alkenyl, $C_{2-6}$alkynyl, —(O—CH$_2$—CH$_2$)$_m$—R$^c$, carbocyclyl, and heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R, —S—R, —O—C(O)—R, —C(O)—R, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$, $C_2$-$C_6$ alkenyl, $R^{ay}$, and $C_{1-6}$alkyl that is optionally substituted with one or more groups independently selected from oxo and halo;

each $R^b$ is independently selected from oxo, $C_{1-6}$alkyl, $C_{2-6}$alkenyl, $C_{2-6}$alkynyl, $-(O-CH_2-CH_2)_m-R^d$, carbocyclyl, heterocyclyl, halo, $-NO_2$, $-N(R^w)_2$, $-CN$, $-C(O)-N(R^w)_2$, $-S(O)-N(R^w)_2$, $-S(O)_2-N(R^w)_2$, $-O-R^w$, $-S-R^w$, $-O-C(O)-R^w$, $-O-C(O)-O-R^w$, $-C(O)-R^w$, $-C(O)-O-R^w$, $-S(O)-R^w$, $-S(O)_2-R^w$, $-O-C(O)-N(R^w)_2$, $-N(R^w)-C(O)-OR^w$, $-N(R^w)-C(O)-N(R^w)_2$, $-N(R^w)-C(O)-R^w$, $-N(R^w)-S(O)-R^w$, $-N(R^w)-S(O)_2-R^w$, $-N(R^w)-S(O)-N(R^w)_2$, and $-N(R^w)-S(O)_2-N(R^w)_2$, wherein any $C_{1-6}$alkyl, $C_{2-6}$alkenyl, $C_{2-6}$alkynyl, $-(O-CH_2-CH_2)_m-R^d$, carbocyclyl, and heterocyclyl is optionally substituted with one or more groups independently selected from oxo, halo, $-NO_2$, $-N(R^w)_2$, $-CN$, $-C(O)-N(R^w)_2$, $-S(O)-N(R^w)_2$, $-S(O)_2-N(R^w)_2$, $-O-R^w$, $-S-R^w$, $-O-C(O)-R^w$, $-C(O)-R^w$, $-C(O)-O-R^w$, $-S(O)-R^w$, $-S(O)_2-R^w$, $-C(O)-N(R^w)_2$, $-N(R^w)-C(O)-R^w$, $-N(R^w)-S(O)-R^w$, $-N(R^w)-S(O)_2-R^w$, $C_2-C_6$ alkenyl, $R^y$, and $C_{1-6}$alkyl that is optionally substituted with one or more groups independently selected from oxo and halo;

each $R^c$ is independently selected from hydrogen, halo, $C_{1-6}$alkyl, $C_{2-6}$alkenyl, $C_2$-6alkynyl, carbocyclyl, and heterocyclyl, wherein each $C_{1-6}$alkyl, $C_{2-6}$alkenyl, $C_{2-6}$alkynyl, carbocyclyl and heterocyclyl is optionally substituted with one or more groups independently selected from halo, hydroxy, and $C_{1-6}$alkoxy;

each $R^d$ is independently selected from hydrogen, halo, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl and heterocyclyl is optionally substituted with one or more groups independently selected from halo, hydroxy, and $C_{1-6}$alkoxy;

each $R^v$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from oxo, cyano, nitro, halo, $-N(R^{ax})_2$, $-OR^{ax}$, $C_2-C_6$ alkenyl, $R^{ay}$, and $C_1-C_6$ alkyl that is optionally substituted with one or more groups independently selected from oxo and halo; or two $R^v$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^w$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from oxo, cyano, nitro, halo, $-N(R^x)_2$, $-OR^x$, $C_2-C_6$ alkenyl, $R^y$, and $C_1-C_6$ alkyl that is optionally substituted with one or more groups independently selected from oxo and halo; or two $R^w$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^x$ is independently selected from hydrogen and $C_{1-6}$alkyl;

each $R^{ax}$ is independently selected from hydrogen and $C_{1-6}$alkyl;

each $R^y$ is aryl that is optionally substituted with one or more groups independently selected from halo, hydroxyl, cyano, nitro, amino, $-O-S(O)_2-R^z$, $-OSi(R^z)_3$, and $-O$-(heterocyclyl);

each $R^{ay}$ is aryl that is optionally substituted with one or more groups independently selected from halo, hydroxyl, cyano, nitro, amino, $-O-S(O)_2-R^{az}$, $-OSi(R^{az})_3$, and $-O$-(heterocyclyl);

each $R^z$ is independently selected from $C_{1-6}$alkyl and aryl;

each $R^{az}$ is independently selected from $C_{1-6}$alkyl and aryl;

each m is 1, 2, 3, 4, or 5; and each n is 1, 2, 3, 4, or 5;

wherein the compound of formula (I) and formula (V) optionally comprises one or more imaging isotopes;

wherein one or more carbon atoms of the compound of formula (I) and formula (V) is deuterated; and wherein the compound of formula (V) is optionally substituted with one or more groups $R^a$. In some embodiments, formula (V) is substituted with one or more groups $R^a$.

Another aspect includes a pharmaceutical composition comprising a deuterated compound as described herein, or a pharmaceutically acceptable salt thereof, and a pharmaceutically acceptable diluent or carrier.

Another aspect includes a method for detecting neurofibrillary tangles and/or senile plaques in an animal comprising administering a deuterated compound comprising an imaging isotope as described herein, or a pharmaceutically acceptable salt thereof, to the animal, and measuring the radioactive signal of the compound.

Another aspect includes a method of detecting a neurological disorder associated with amyloid plaque and/or tau protein aggregation in an animal comprising administering a deuterated compound comprising an imaging isotope as described herein, or a pharmaceutically acceptable salt thereof, to the animal, and measuring the radioactive signal of the compound, which is associated with amyloid deposits and/or tau protein aggregates.

Another aspect includes a method of detecting Alzheimer's disease associated with amyloid plaque and/or tau protein aggregation in an animal comprising administering a deuterated compound comprising an imaging isotope as described herein, or a pharmaceutically acceptable salt thereof, to the animal, and measuring the radioactive signal of the compound associated with amyloid deposits and/or tau protein aggregates.

Another aspect includes a method of detecting Alzheimer's disease associated with tau protein aggregation comprising administering a deuterated compound comprising an imaging isotope as described herein, or a pharmaceutically acceptable salt thereof, to the animal, and measuring the radioactive signal of the compound associated with tau protein aggregates.

Another aspect includes a deuterated compound as described herein, or a pharmaceutically acceptable salt thereof, for use in medical diagnosis or treatment.

Another aspect includes a deuterated compound as described herein, or a pharmaceutically acceptable salt thereof, for use in detecting neurofibrillary tangles and/or senile plaques.

Another aspect includes a deuterated compound as described herein, or a pharmaceutically acceptable salt thereof, for use in detecting a neurological disorder.

Another aspect includes a deuterated compound as described herein, or a pharmaceutically acceptable salt thereof, for use in detecting Alzheimer's disease.

Another aspect includes the use of a deuterated compound as described herein, or a pharmaceutically acceptable salt thereof, to prepare a medicament for detecting neurofibrillary tangles and/or senile plaques in an animal.

Another aspect includes the use of a deuterated compound as described herein, or a pharmaceutically acceptable salt thereof, to prepare a medicament for detecting a neurological disorder in an animal.

Another aspect includes the use of a deuterated compound as described herein, or a pharmaceutically acceptable salt thereof, to prepare a medicament for detecting Alzheimer's disease in an animal.

Another aspect includes a method of detecting progressive supranuclear palsy associated with amyloid plaque and/or tau protein aggregation in an animal, comprising administering a deuterated compound comprising an imaging isotope as described herein, or a pharmaceutically acceptable salt thereof, to the animal, and measuring the radioactive signal of the compound associated with amyloid deposits and/or tau protein aggregates.

Another aspect includes a method of detecting progressive supranuclear palsy associated with tau protein aggregation, comprising administering a deuterated compound comprising an imaging isotope as described herein, or a pharmaceutically acceptable salt thereof, to the animal, and measuring the radioactive signal of the compound associated with tau protein aggregates.

BRIEF DESCRIPTION OF THE FIGURES

FIGS. 4A-4F: Pre-clinical PET imaging in mice from Example 6 below.

DETAILED DESCRIPTION

Compounds and Definitions

Figure 1:
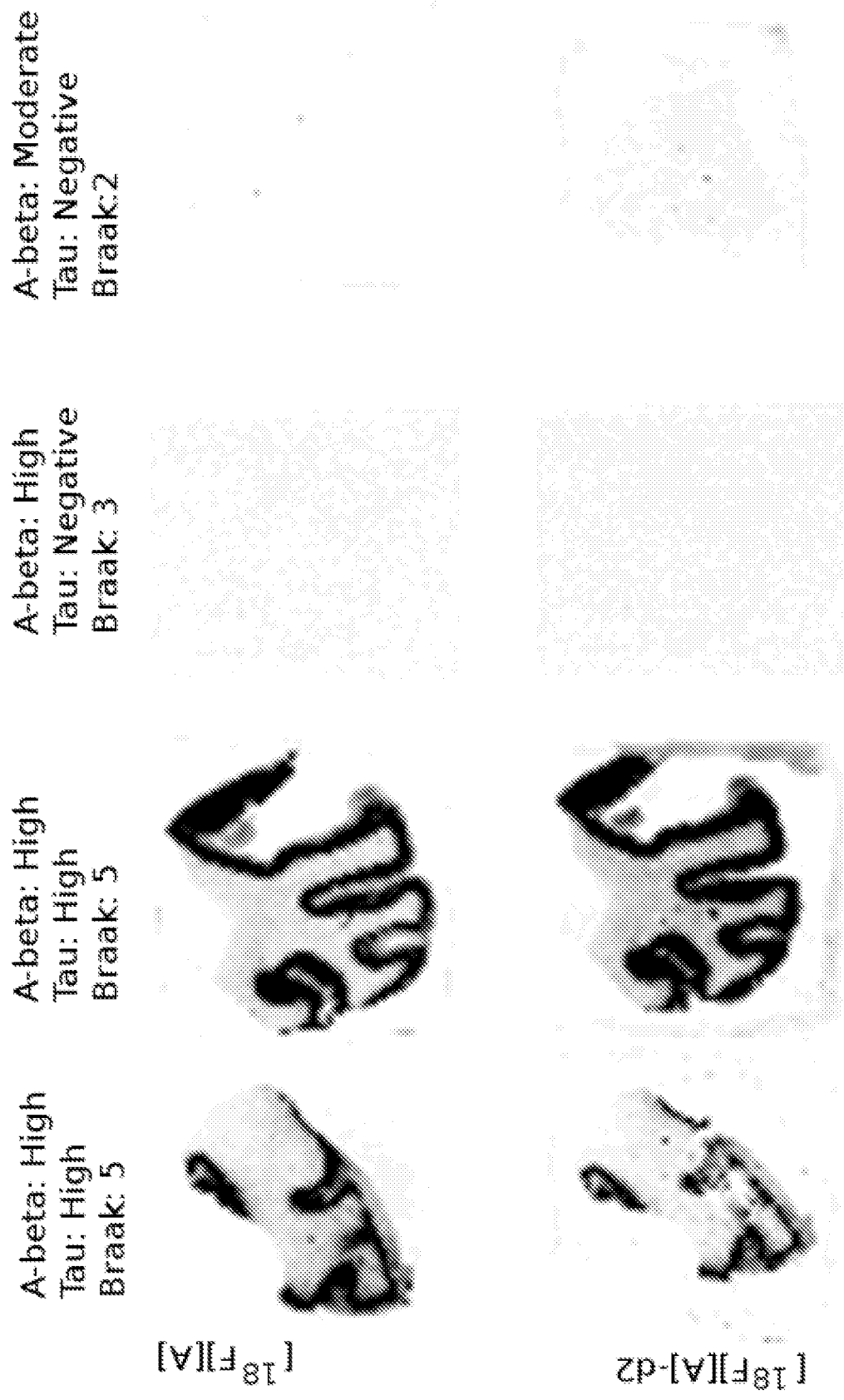
FIG. 1: Autoradiographic evaluation of binding properties of [A] and [A]-d2 using human brain tissues.

Definitions and terms are described in more detail below. Chemical elements are identified in accordance with the Periodic Table of the Elements, CAS version, *Handbook of Chemistry and Physics*, 75$^{th}$ Ed.

Unless otherwise stated, the a compounds include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds, wherein the independent replacement or enrichment of one or more hydrogen by deuterium or tritium, carbon by $^{13}$C- or $^{14}$C carbon, nitrogen by a $^{15}$N nitrogen, sulfur by a $^{33}$S, $^{34}$S or $^{36}$S sulfur, or oxygen by a $^{17}$O or $^{18}$O oxygen are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., Tetrahedron 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, IN 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O or (=O)$_2$.

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptanyl, bicyclo[2.2.2]octanyl, naphthalenyl, and bicyclo[3.2.2]nonanyl; and spiro carbocyclyls include spiro[2.2]pentanyl, spiro[2.3]hexanyl, spiro[2.4]heptanyl, spiro[2.5]octanyl and spiro[4.5]decanyl. The term carbocyclyl includes aryl ring systems as defined herein. The term carbocycyl also includes cycloalkyl rings (e.g., saturated or partially unsaturated mono-, bi-, or spiro-carbocycles).

The term "alkyl," as used herein, refers to a saturated linear or branched-chain monovalent hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), heptyl, octyl, nonyl, decyl, undecyl and dodecyl.

The term "alkenyl," as used herein, denotes a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched monovalent hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched monovalent radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g., 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted byone or more substituents described herein. A particular aryl is phenyl. In another embodiment aryl includes an aryl ring fused to one or more carbocyclic rings, such as indanyl, phthalimidyl, naphthimidyl, phenantriidinyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. In another embodiment, heteroaryl includes bicyclic or tricyclic aromatic groups where one or more ring atoms (e.g., 1, 2, 3, 4, 5, 6, 7, or 8) is nitrogen, sulfur or oxygen that is independently optionally substituted. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-onyl. A heteroaryl group may be mono-, bi- or tri-cyclic.

As used herein, the term "heterocyclyl" refers to a "carbocyclyl" as defined herein, wherein one or more (e.g., 1, 2, 3, or 4) carbon atoms have been replaced with a heteroatom (e.g., O, N, or S). In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein. In one embodiment, heterocyclyl includes 5-6 membered monocyclic cyclic groups where one or more ring atoms is nitrogen, sulfur or oxygen (e.g., 1, 2, 3 or 4) that is independently optionally substituted. In another embodiment, heterocyclyl includes bicyclic or tricyclic groups where one or more ring atoms (e.g., 1, 2, 3, 4, 5, 6, 7, or 8) is nitrogen, sulfur or oxygen that is independently optionally substituted.

In one example, heterocyclyl includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, and 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As between chemical names and structures shown, if there are any discrepancies, the structure prevails.

Throughout this application, the term "about" is used to indicate that a value includes the standard deviation of error for the device and/or method being employed to determine the value.

As used herein, "a" or "an" means one or more, unless clearly indicated otherwise. As used herein, "another" means at least a second or more.

Imaging Isotopes and Imaging

Diagnostic techniques in nuclear medicine use radioactive tracers which emit gamma rays from within the body. These tracers are generally short-lived isotopes linked to chemical compounds which permit specific physiological processes to be scrutinized. They can be given by injection, inhalation or orally. The first type is where single photons are detected by a gamma camera which can view organs from many different angles. The camera builds up an image from the points from which radiation is emitted; this image is enhanced by a computer and viewed by a physician on a monitor for indications of abnormal conditions.

Positron Emission Tomography (PET) is a precise and sophisticated technique using isotopes produced in a cyclotron. A positron-emitting radionuclide is introduced, usually by injection, and accumulates in the target tissue. As it decays it emits a positron, which promptly combines with a nearby electron resulting in the simultaneous emission of two identifiable gamma rays in opposite directions. These are detected by a PET camera and give a very precise indication of their origin. PET's most important clinical role is in oncology, with fluorine-18 as the tracer, since it has proven to be the most accurate non-invasive method of detecting and evaluating most cancers. It is also well used in cardiac and brain imaging.

A number of medical diagnostic procedures, including PET and SPECT, utilize radiolabeled compounds and are well known in the art. PET and SPECT are very sensitive techniques and require small quantities of radiolabeled compounds, called tracers. The labeled compounds are transported, accumulated and converted in vivo in a similar manner as the corresponding non-radioactively labeled compound. Tracers, or probes, can be radiolabeled with a radionuclide useful for PET imaging, such as $^{11}C$, $^{13}N$, $^{15}O$, $^{18}F$, $^{64}Cu$, and $^{124}I$, or with a radionuclide useful for SPECT imaging, such as $^{99}Tc$, $^{77}Br$, $^{61}Cu$, $^{153}Gd$, $^{123}I$, $^{125}I$, $^{131}I$ and $^{32}P$. These are examples of "imaging isotopes," as that term is used herein.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

According to another embodiment, the present invention is also directed at a method of imaging amyloid deposits and NTFs. When the compounds of this invention are used as imaging agents, they are labeled with one or more suitable imaging isotopes (e.g., radioactive isotopes, radiolabels or radioactive labels), for example, radioactive halogens, such as $^{18}F$ and/or with one or more radioactive metals.

Regarding radiohalogens, $^{125}I$ isotopes are useful for laboratory testing but they will generally not useful for diagnostic purposes because of the relatively long half-life (60 days) and low gamma-emission (30-65 keV) of $^{125}I$. The isotope $^{123}I$ has a half-life of thirteen hours and gamma energy of 159 keV, and it is therefore typical that labeling of ligands to be used for diagnostic purposes would be with this isotope or with $^{18}F$ (half-life of 2 hours). Other imaging isotopes which may be used include $^{131}I$, $^{77}Br$ and $^{76}Br$.

In another embodiment, compounds of the present invention contain a radioactive isotope of carbon as the radiolabel. This refers to a compound that comprises one or more radioactive carbon atoms, preferably $^{11}C$, with a specific activity above that of the background level for that atom. It is well known that naturally occurring elements are present in the form of varying isotopes, some of which are radioactive. The radioactivity of the naturally occurring elements is a result of the natural distribution or abundance of these isotopes, and is commonly referred to as a background level. The carbon labeled compounds of the present invention have a specific activity that is higher than the natural abundance, and therefore above the background level. The carbon labeled compositions of the present invention can be used for tracing, imaging, radiotherapy, and the like.

Those skilled in the art are familiar with the various ways to detect labeled compounds for imaging purposes. For example, positron emission tomography (PET) or single photon emission computed tomography (SPECT) can be used to detect radiolabeled compounds. The label that is introduced into the compound can depend on the detection method desired. Those skilled in the art are familiar with PET detection of a positron-emitting atom, such as $^{18}F$. The present invention is also directed to specific compounds described herein where the $^{18}F$ atom is replaced with a non-radiolabeled fluorine atom. Those skilled in the art are familiar with SPECT detection of a photon-emitting atom, such as $^{123}I$ or $^{99m}Tc$.

The radioactive diagnostic or detection agent should have sufficient radioactivity and radioactivity concentration which can assure reliable diagnosis and detection. The desired level of radioactivity can be attained by the methods provided herein for preparing compounds. The imaging of amyloid deposits and NTFs can also be carried out quantitatively so that the amount of amyloid deposits and NTFs can be determined.

Typically, a prerequisite for an in vivo imaging agent of the brain is the ability to cross the intact blood-brain barrier. In a first step of a method of imaging, a labeled compound is introduced into a tissue or a patient in a detectable quantity. The compound is typically part of a pharmaceutical composition and is administered to the tissue or the patient by methods well known to those skilled in the art. Typically, administration is intravenously.

In other embodiments of the invention, the labeled compound is introduced into a patient in a detectable quantity and after sufficient time has passed for the compound to become associated with amyloid deposits and/or tau proteins, the labeled compound is detected noninvasively. In another embodiment of the invention, a labeled compound is introduced into a patient, sufficient time is allowed for the compound to become associated with amyloid deposits, and then a sample of tissue from the patient is removed and the labeled compound in the tissue is detected apart from the patient. In another embodiment of the invention, a tissue sample is removed from a patient and a labeled compound is introduced into the tissue sample. After a sufficient amount of time for the compound to become bound to amyloid deposits and/or tau proteins, the compound is detected.

A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The amount of time necessary can easily be determined by introducing a detectable amount of a labeled compound into a patient and then detecting the labeled compound at various times after administration.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

One or more imaging isotopes can be incorporated into a compound of formula (I) by replacing one or more atoms (e.g., hydrogen or carbon atoms) in the compound of formula (I) or formula (V) with an imaging isotope. The incorporation of an imaging isotope can be carried out using known techniques. For example, techniques may be based on nucleophilic or electrophilic $^{18}$F-fluorination of suitable precursors as reviewed, for example, in Medicinal Chemistry Approaches to Personalized Medicine (Lackey, Roth Eds), Chapter 12 (Wiley-VCH, ISBN 978-3-527-33394-3). See also U.S. Patent Application No. 2011/0182812, incorporated herein by reference in its entirety.

Deuterated

The term "deuterated" means enriched in deuterium above its natural abundance at one or more positions of a compound. When a particular position, for example, a carbon atom, is deuterated, it is understood that the abundance of deuterium at that position is substantially greater than the natural abundance of deuterium, which is 0.015%. A deuterated position typically has a minimum isotopic enrichment factor of at least 3000 (45% deuterium incorporation).

The term "isotopic enrichment factor" as used herein means the ratio between the isotopic abundance and the natural abundance of a specified isotope. In certain embodiments, a compound has an isotopic enrichment factor of at least 3500 (52.5% deuterium incorporation) at a given deuterated atom, at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In some embodiments, 100% deuterium incorporation is achieved.

It is to be understood that a deuterated compound contains one or more deuterium atoms. For example, a deuterated compound may contain just one deuterium. In some embodiments, a deuterated compound contains just two deuteriums. In some embodiments, a deuterated compound contains only three deuteriums. In some embodiments, a deuterated compound contains four deuteriums. In some embodiments, a deuterated compound contains 1, 2, 3, or 4 deuteriums, or any range derivable therein.

Deuterium can be incorporated into a compound of formula (I) using a variety of known reagents and synthetic techniques. For example, deuterium can be incorporated into a compound of formula (I) using LiAlD$_4$. It can also be incorporated into a compound of formula (I) such as through reduction, catalytic hydrogenation or isotopic exchange using appropriate deuterated reagetns such as deuterides, D$_2$ and D$_2$O.

Exemplary Values

In certain embodiments the compound is a compound of formula (I) or a salt thereof.

In certain embodiments R$^1$ is a 6-membered heteroaryl ring.

In certain embodiments R$^1$ is:

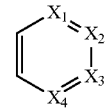

wherein:
X$_1$, X$_2$, X$_3$, and X$_4$ are each independently CH or N; and
wherein R$^1$ is optionally substituted with one or more groups R$^a$.

In certain embodiments R$^1$ is phenyl, pyridyl, or pyrimidyl.

In certain embodiments R$^1$ is a 9- or 10-membered bicyclic heteroaryl ring.

In certain embodiments R$^1$ is a 9- or 10-membered bicyclic heteroaryl ring that comprises one or more nitrogens.

In certain embodiments R$^1$ is a 9- or 10-membered bicyclic heteroaryl ring that comprises two or more nitrogens.

In certain embodiments R$^1$ is a 9- or 10-membered bicyclic heteroaryl ring that comprises one or more nitrogens and one or more oxygens.

In certain embodiments R$^1$ is:

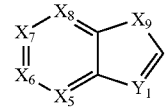

wherein:
X$_5$, X$_6$, X$_7$, and X$_8$ are each independently CH or N;
X$_9$ is CH$_2$, NH, O, or S; and
Y$_1$ is CH, or N;

wherein $R^1$ is optionally substituted with one or more groups $R^a$.

In certain embodiments $R^1$ is:

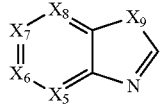

wherein:

$X_5$, $X_6$, $X_7$, and $X_8$ are each independently CH or N; and $X_9$ is $CH_2$, NH, O, or S;

wherein $R^1$ is optionally substituted with one or more groups $R^a$.

In certain embodiments $R^1$ is:

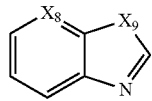

wherein:

$X_8$ is CH or N; and $X_9$ is $CH_2$, NH, O, or S; wherein $R^1$ is optionally substituted with one or more groups $R^a$.

In certain embodiments $X_9$ is $CH_2$.

In certain embodiments $X_9$ is O.

In certain embodiments $X_9$ is S.

In certain embodiments $R^1$ is:

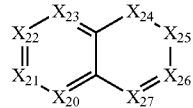

wherein:

$X_{20}$-$X_{27}$ are each independently CH or N;

wherein $R^1$ is optionally substituted with one or more groups $R^a$.

In certain embodiments $R^1$ is:

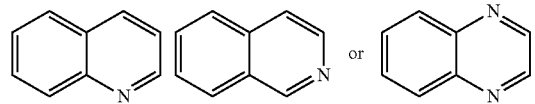

wherein $R^1$ is optionally substituted with one or more groups $R^a$.

In certain embodiments $R^1$ is a 12-13 membered tricyclic heterocyclyl that comprises one or more nitrogens.

In certain embodiments $R^1$ is a 12-13 membered tricyclic heterocyclyl that comprises two or more nitrogens.

In certain embodiments $R^1$ is a 12-13 membered tricyclic heterocyclyl that comprises three or more nitrogens.

In certain embodiments $R^1$ is:

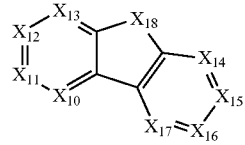

wherein:

each $X_{10}$-$X_{17}$ is independently CH or N; and $X_{18}$ is $CH_2$, NH, O, or S;

wherein $R^1$ is optionally substituted with one or more groups $R^a$.

In certain embodiments $R^1$ is:

wherein:

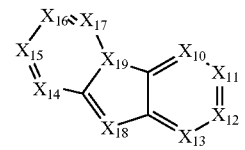

each $X_{10}$-$X_{17}$ is independently CH or N;

$X_{18}$ is CH or N; and $X_{19}$ is CH or N;

wherein $R^1$ is optionally substituted with one or more groups $R^a$.

In certain embodiments $R^1$ is:

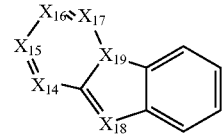

wherein:

each $X_{14}$—$X_{17}$ is independently CH or N;

$X_{18}$ is CH or N; and $X_{19}$ is CH or N;

wherein $R^1$ is optionally substituted with one or more groups $R^a$.

In certain embodiments $R^1$ is:

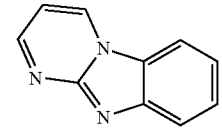 [SMILES: c1ccc2c(c1)nc1ncccn12]

and is optionally substituted with one or more groups $R^a$.

In certain embodiments $R^1$ is:

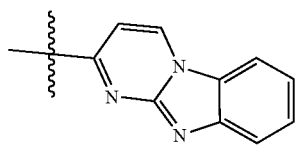 [SMILES: *c1ccn2c(n1)nc1ccccc12]

and is optionally substituted with one or more groups $R^a$.

In certain embodiments $R^1$ is:

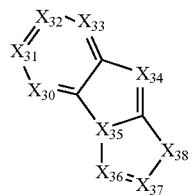

wherein:
each $X_{30}$-$X_{37}$ is independently CH or N; and
$X_{38}$ is $CH_2$, NH, O, or S;
wherein $R^1$ is optionally substituted with one or more groups $R^a$.

In certain embodiments A is absent.

In certain embodiments A is ethynyl;

In certain embodiments $R^2$ is a 6-membered carbocyclyl that is optionally substituted with one or more groups $R^b$.

In certain embodiments $R^2$ is cyclohexyl or phenyl, which cyclohexyl and phenyl is optionally substituted with one or more groups $R^b$.

In certain embodiments $R^2$ is pyrrolyl, thiophenyl, imidazolyl, thiazolyl, oxazolyl, pyrazolyl, isoxazolyl, isothiazolyl, morpholinyl, piperidinyl, piperazinyl, pyrrolidinyl, pyridinyl, pyrimidinyl, pyrazinyl, 3-azabicyclo[3.1.0]hexanyl, or pyridazinyl, which $R^2$ is optionally substituted with one or more groups $R^b$.

In certain embodiments the compound is a compound of formula (V), or a salt thereof.

In certain embodiments the compound is a compound of formula (Va):

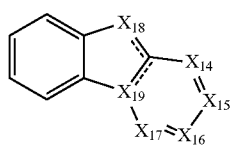

(Va)

or a salt thereof, wherein the compound of formula (Va) is substituted with one or more groups $R^a$.

In certain embodiments the compound comprises an imaging isotope.

In certain embodiments the imaging isotope is $^{18}F$.

In certain embodiments the compound is a compound having the formula (Ia):

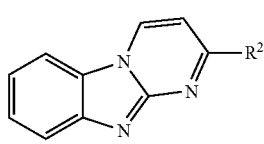

(Ia)

or a salt thereof, wherein:
$R^2$ is 6-membered carbocyclyl or a 5- or 6-membered heterocyclyl, which carbocyclyl and heterocyclyl is optionally substituted with one or more groups $R^b$;
each $R^b$ is independently selected from $C_{1-6}$alkyl, $C_{2-6}$alkenyl, $C_{2-6}$alkynyl, —(O—$CH_2$—$CH_2$)$_m$—$R^d$, carbocyclyl, heterocyclyl, —F, —Cl, —Br, —I, —$NO_2$, —N($R^w$)$_2$, —CN, —C(O)—N($R^w$)$_2$, —O—$R^w$, —O—C(O)—$R^w$, —C(O)—$R^w$, and —C(O)—O—$R^w$, wherein any $C_{1-6}$alkyl, $C_{2-6}$alkenyl, $C_{2-6}$alkynyl, —(O—$CH_2$—$CH_2$)$_m$—$R^d$, carbocyclyl, and heterocyclyl is optionally substituted with one or more groups independently selected from oxo, halo, —O—$R^w$, —O—C(O)—$R^w$, —C(O)—$R^w$, —C(O)—O—$R^w$, —C(O)—N($R^w$)$_2$, and —N($R^w$)—C(O)—$R^w$.

In certain embodiments the compound is a compound having formula (Ia):

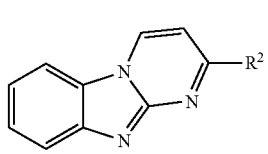

(Ia)

or a salt thereof, wherein:
$R^2$ is piperidinyl or 3-azabicyclo[3.1.0]hexanyl, which piperidinyl and 3-azabicyclo[3.1.0]hexanyl is optionally substituted with one or more groups $R^b$; and each $R^b$ is independently selected from $C_{1-6}$alkyl, $C_{2-6}$alkenyl, $C_{2-6}$alkynyl, —(O—$CH_2$—$CH_2$)$_m$—$R^d$, carbocyclyl, heterocyclyl, —F, —Cl, —Br, —I, —$NO_2$, —N($R^w$)$_2$, —CN, —C(O)—N($R^w$)$_2$, —O—$R^w$, —O—C(O)—$R^w$, —C(O)—$R^w$, and —C(O)—O—$R^w$, wherein any $C_{1-6}$alkyl, $C_{2-6}$alkenyl, $C_{2-6}$alkynyl, —(O—$CH_2$—$CH_2$)$_m$—$R^d$, carbocyclyl, and heterocyclyl is optionally substituted with one or more groups independently selected from oxo, halo, —O—$R^w$, —O—C(O)—$R^w$, —C(O)—$R^w$, —C(O)—O—$R^w$, —C(O)—N($R^w$)$_2$, and —N($R^w$)—C(O)—$R^w$.

In certain embodiments the compound is a compound having formula (Ib):

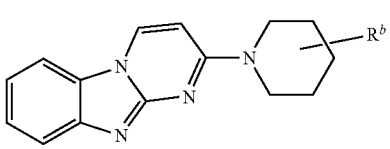

(Ib)

or a salt thereof, wherein:
$R^b$ is deuterated and is selected from $C_{1-6}$alkyl, $C_{2-6}$alkenyl, $C_{2-6}$alkynyl, —(O—$CH_2$—$CH_2$)$_m$—$R^d$, carbocyclyl, heterocyclyl, —N($R^w$)$_2$, —C(O)—N($R^w$)$_2$, —O—$R^w$, —O—C(O)—$R^w$, —C(O)—$R^w$, and —C(O)—O—$R^w$, wherein any $C_{1-6}$alkyl, $C_{2-6}$alkenyl, $C_{2-6}$alkynyl, —(O—$CH_2$—$CH_2$)$_m$—$R^d$, carbocyclyl, and heterocyclyl is optionally substituted with one or more groups independently selected from oxo, halo, —O—$R^w$, —O—C(O)—$R^w$, —C(O)—$R^w$, —C(O)—O—$R^w$, —C(O)—N($R^w$)$_2$, and —N($R^w$)—C(O)—$R^w$; and $R^b$ comprises one or more imaging isotopes.

In certain embodiments the compound is a compound having formula (Ic):

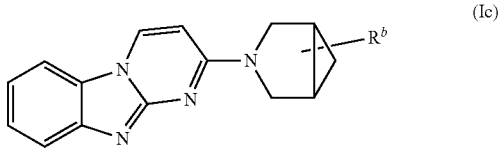

(Ic)

or a salt thereof, wherein:

$R^b$ is deuterated and is selected from $C_{1-6}$alkyl, $C_{2-6}$alkenyl, $C_{2-6}$alkynyl, —(O—CH$_2$—CH$_2$)$_m$—R$^d$, carbocyclyl, heterocyclyl, —N(R$^w$)$_2$, —C(O)—N(R$^w$)$_2$, —O—R$^w$, —O—C(O)—R$^w$, —C(O)—R$^w$, and —C(O)—O—R$^w$, wherein any $C_{1-6}$alkyl, $C_{2-6}$alkenyl, $C_{2-6}$alkynyl, —(O—CH$_2$—CH$_2$)$_m$—R$^d$, carbocyclyl, and heterocyclyl is optionally substituted with one or more groups independently selected from oxo, halo, —O—R$^w$, —O—C(O)—R$^w$, —C(O)—R$^w$, —C(O)—O—R$^w$, —C(O)—N(R$^w$)$_2$, and —N(R$^w$)—C(O)—R$^w$; and $R^b$ comprises one or more imaging isotopes.

In certain embodiments the compound is a compound having formula (Id):

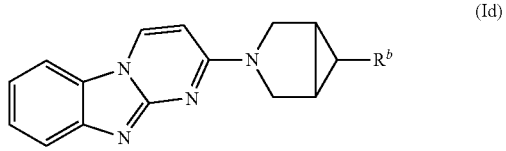

(Id)

or a salt thereof, wherein:

$R^b$ is deuterated and is selected from $C_{1-6}$alkyl, $C_{2-6}$alkenyl, $C_{2-6}$alkynyl, —(O—CH$_2$—CH$_2$)$_m$—R$^d$, carbocyclyl, heterocyclyl, —N(R$^w$)$_2$, —C(O)—N(R$^w$)$_2$, —O—R$^w$, —O—C(O)—R$^w$, —C(O)—R$^w$, and —C(O)—O—R$^w$, wherein any $C_{1-6}$alkyl, $C_{2-6}$alkenyl, $C_{2-6}$alkynyl, —(O—CH$_2$—CH$_2$)$_m$—R$^d$, carbocyclyl, and heterocyclyl is optionally substituted with one or more groups independently selected from oxo, halo, —O—R$^w$, —O—C(O)—R$^w$, —C(O)—R$^w$, —C(O)—O—R$^w$, —C(O)—N(R$^w$)$_2$, and —N(R$^w$)—C(O)—R$^w$; and $R^b$ comprises one or more imaging isotopes.

In certain embodiments each $R^a$ is independently selected from $C_{1-6}$alkyl, $C_{2-6}$alkenyl, $C_{2-6}$alkynyl, and —O—R$^v$; and each R$^v$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected —OR$^{ax}$.

In certain embodiments each $R^a$ is independently selected from —O—R$^v$; and each R$^v$ is independently selected from hydrogen, $C_{1-6}$alkyl, $C_{2-6}$alkenyl, $C_{2-6}$alkynyl, and carbocyclyl.

In certain embodiments each $R^a$ is independently selected from —O—CH$_3$.

In certain embodiments each $R^b$ is independently selected from $C_{1-6}$alkyl, $C_{2-6}$alkenyl, $C_{2-6}$alkynyl, and —O—R$^w$, wherein any $C_{1-6}$alkyl, $C_{2-6}$alkenyl, and $C_{2-6}$alkynyl, is optionally substituted with one or more groups independently selected from —O—R$^w$; and each R$^w$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from —OR$^x$; wherein at least one $R^b$ is deuterated and comprises one or more imaging isotopes.

In certain embodiments each $R^b$ is $C_{1-6}$alkyl that is optionally substituted with one or more groups independently selected from —O—R$^w$; and each R$^w$ is independently selected from $C_{1-6}$alkyl; wherein at least one $R^b$ is deuterated and comprises one or more imaging isotopes.

In certain embodiments $R^b$ is a $C_{1-6}$alkyl group that comprises one or more imaging isotopes.

In certain embodiments $R^b$ is a $C_{1-6}$alkyl group that comprises an imaging isotope $^{18}$F.

In certain embodiments the compound comprises a carbon atom that is both deuterated and covalently bonded to an imaging isotope.

In certain embodiments $R^b$ is —CH$_2$—*CD$_2$-$^{18}$F, wherein the carbon marked * is deuterated.

In certain embodiments $R^b$ is —CH$_2$—*CD$_2$-$^{18}$F, wherein the carbon marked * has a deuterium isotopic enrichment factor of at least 3500.

In certain embodiments $R^b$ is —CH$_2$—*CD$_2$-$^{18}$F, wherein the carbon marked * has a deuterium isotopic enrichment factor of at least 6000.

In certain embodiments $R^b$ is —CH$_2$—CH$_2$—O—*CD$_2$-*CD$_2$-$^{18}$F, wherein each carbon marked * is deuterated.

In certain embodiments $R^b$ is —CH$_2$—CH$_2$—O—*CD$_2$-*CD$_2$-$^{18}$F, wherein each carbon marked * has a deuterium isotopic enrichment factor of at least 3500.

In certain embodiments $R^b$ is —CH$_2$—CH$_2$—O—*CD$_2$-*CD$_2$-$^{18}$F, wherein each carbon marked * has a deuterium isotopic enrichment factor of at least 6000.

In certain embodiments the compound is a compound having the formula (Ie):

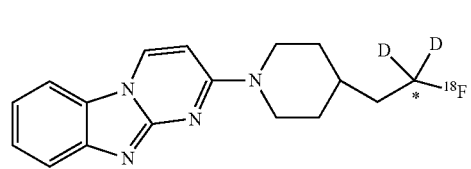

(Ie)

wherein the carbon marked * has a deuterium isotopic enrichment factor of at least 3500. In certain embodiments the carbon marked * has a deuterium isotopic enrichment factor of at least 4000. In certain embodiments the carbon marked * has a deuterium isotopic enrichment factor of at least 4500. In certain embodiments the carbon marked * has a deuterium isotopic enrichment factor of at least 5000. In certain embodiments the carbon marked * has a deuterium isotopic enrichment factor of at least 5500. In certain embodiments the carbon marked * has a deuterium isotopic enrichment factor of at least 6000. In certain embodiments the carbon marked * has a deuterium isotopic enrichment factor of at least 6333.3. In certain embodiments the carbon marked * has a deuterium isotopic enrichment factor of at least 6466.7. In certain embodiments the carbon marked * has a deuterium isotopic enrichment factor of at least 6600. In certain embodiments the carbon marked * has a deuterium isotopic enrichment factor of at least 6633.3. In some embodiments, 100% deuterium incorporation is achieved with respect to the carbon marked * in the compound of formula (Ie).

In certain embodiments the compound is a compound having the formula:

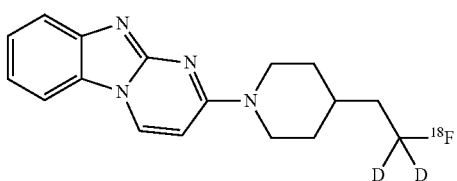 [SMILES: [2H]C([2H])([18F])CC1CCN(c2ccn3c(n2)nc2ccccc23)CC1]

or a salt thereof. In certain embodiments the compound is a compound selected from:

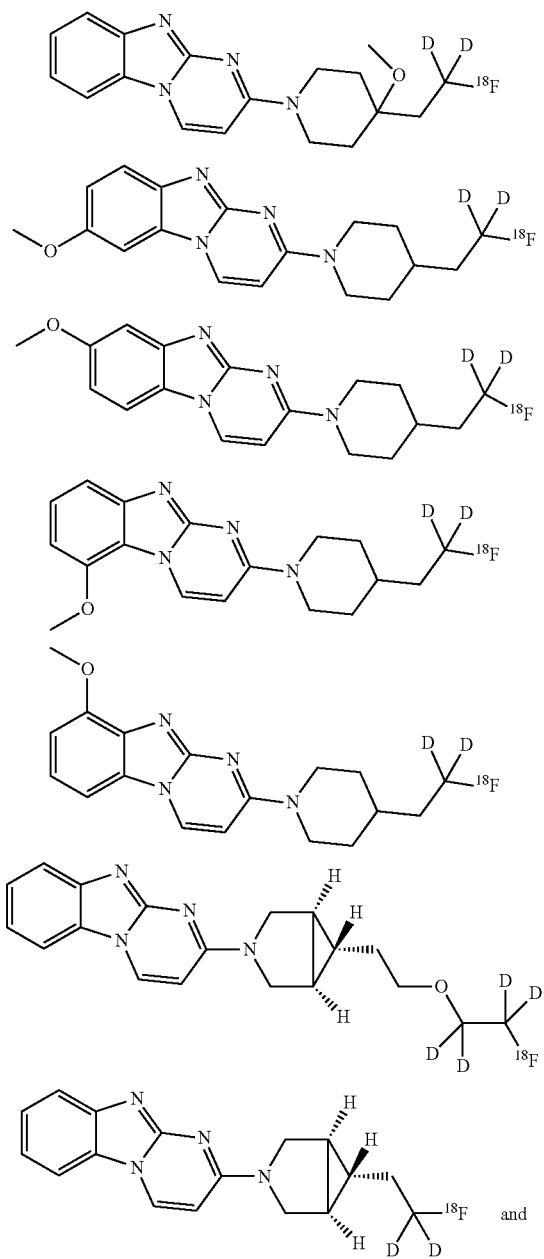

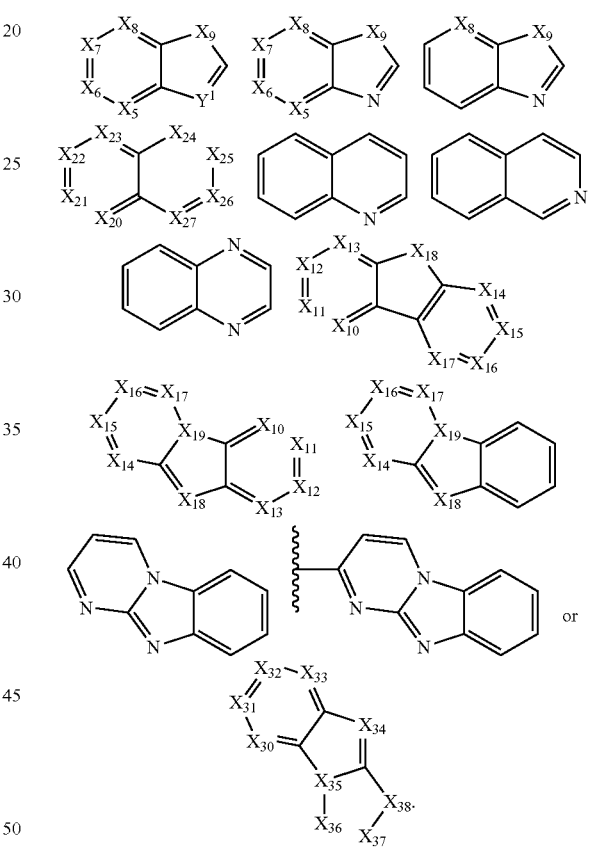

and salts thereof.

R¹ can be attached to the remainder of a compound of formula (I) through any synthetically feasible position. For example, when R¹ has one of the following values, it can be attached to the remainder of a compound of formula (I) through any synthetically feasible position:

For example, in one embodiment, a hydrogen atom can be removed from a carbon or nitrogen atom in R¹ to provide an open valence that can form the covalent bond with the remainder of a compound of formula (I).

Indications

Compounds of the present invention may be used in a variety of contexts, such as imaging and detection contexts. In certain embodiments, the compound is introduced into patients who suffer from or are at risk of developing a neurological disorder. In certain embodiments, the neurological disorder is associated with the development of amyloid plaques and/or tau protein aggregates and/or NFTs.

A "neurological disorder" as used herein refers to a disease or disorder which affects the CNS and/or which has an etiology in the CNS. Exemplary CNS diseases or disorders include, but are not limited to, neuropathy, amyloidosis, cancer, an ocular disease or disorder, viral or microbial infection, inflammation, ischemia, neurodegenerative disease, seizure, behavioral disorders, and a lysosomal storage disease. For the purposes of this application, the CNS will be understood to include the eye, which is normally sequestered from the rest of the body by the blood-retina barrier. Specific examples of neurological disorders include, but are not limited to, neurodegenerative diseases including, but not limited to, Lewy body disease, postpoliomyelitis syndrome, Shy-Draeger syndrome, olivopontocerebellar atrophy, Parkinson's disease, multiple system atrophy, striatonigral degeneration, prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), and cancer (e.g., of the CNS, including brain metastases resulting from cancer elsewhere in the body). Tauopathies are also encompassed by the term "neurological disorder" and refer to tau-related disorders or conditions that may overlap with one or more of the conditions noted above. Non-limiting examples of tauopathies include, but are not limited to, Alzheimer's disease, progressive supranuclear palsy, corticobasal degeneration, Pick's disease, stroke, aging, traumatic brain injury, and mild cognitive impairment.

Formulation and Administration

Another aspect includes a pharmaceutical composition comprising a compound of formula (I) or a pharmaceutically acceptable salt thereof. In one embodiment, the composition further comprises a pharmaceutically acceptable carrier or vehicle. In certain embodiments, the composition is formulated for administration to a patient in need thereof.

The term "patient" or "individual" as used herein, refers to an animal, such as a mammal, such as a human. In one embodiment, patient or individual refers to a rodent (e.g., mouse or rat), a dog, or a human.

The term "pharmaceutically acceptable carrier or vehicle" refers to a non-toxic carrier or vehicle that does not destroy the pharmacological activity of the compound with which it is formulated. Pharmaceutically acceptable carriers or vehicles that may be used in the compositions of this invention include, but are not limited to, water, salts, and ethanol Compositions comprising a compound or salt thereof are typically administered intravenously. Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, and saline (e.g., U.S.P. or isotonic sodium chloride solution). In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimens for any particular patient will depend upon a variety of factors, including age, body weight, general health, sex, diet, time of administration, rate of excretion, drug combination, the judgment of the treating physician, and the severity of the particular disease being examined. The amount of a provided compound or salt thereof in the composition will also depend upon the particular compound in the composition.

In one embodiment, a composition comprising a compound of the present invention is administered intravenously in a trace mass amount and a radioactivity amount to permit safe exposure but sufficient to acquire images. In some embodiments, the dosage range is from 5-20 mCi per subject. In some embodiments, the dosage range is about, at least about, or at most about 5, 6, 7, 8, 9, 10, 11, 12, 13, 14, 15, 16, 17, 18, 19, 20, 21, 22, 23, 24, or 25 mCi or more per subject, or any range derivable therein.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

EXAMPLES

General. Common solvents and chemicals were purchased from Aldrich (Milwaukee, WI) or VWR International (Randor, PA), (E)-1,1,1-trichloro-4-ethoxybut-3-en-2-one from PharmaSys (Cary, NC) and t-butyl 4-(2-methoxy-2-oxoethyl)piperidine-1-carboxylate from Santa Cruz Biotechnology Inc. (Santa Cruz, CA). $^{18}$F-Fluoride was purchased from PETNET Solutions (Palo Alto, CA), $^{18}$F Trap & Release Columns (8 mg) were purchased from ORTG, Inc. (Oakdale, TN), and HLB plus sep-pak cartridge from Waters (Milford, MA). Human brain tissue samples were obtained from Banner Sun Health Research Institute (Sun City, AZ), the frozen unfixed samples were sectioned to 5 μm thick samples and stored at −80° C. NMR spectra were acquired on Bruker Avance II 400 spectrometer at 298 K. The $^1$H spectra were recorded at 400 MHz and the chemical shifts are reported in ppm relative to TMS; the $^{19}$F spectra were recorded at 376.3 MHz and the chemical shifts are reported using TFA as an external reference standardized to −76.55 ppm. A Model 521 microwave heater (Resonance Instruments, Skokie, IL) was used for radiochemical reactions. The following systems were used to analyze and purify the products: System A: Analytical LCMS: Waters Acquity UPLC running at 0.7 mL/min. Column: Acquity UPLC BEH C18 1.7 μm 2.1×30 mm. Mobile phase A: water with 0.1% formic acid, B: acetonitrile with 0.1% formic acid, linear gradient 5-95% B in 2 min. The system was equipped with Acquity PDA and Acquity SQ detectors. System B: Preparative HPLC: Waters 2545 pump running at 70 mL/min. Column Phenomenex Gemini-NX 10μ C18 110A AX 100×30.00 mm. Mobile phase A1: water with 0.1 formic acid, A2: water with 0.1% NH₄OH, B: acetonitrile. Linear gradient A1 or A2 to B in 10 min. System D: Semi-preparative HPLC: Agilent 1290, running at 4 mL/min. Column: Phenomenex Luna 5μ C18 100A, 250×10 mm. Mobile phase A: water with 0.1% formic acid, B: acetonitrile with 0.1% formic acid. System E: Analytical LCMS system consisting of HPLC: Pump: Agilent 1290, running at 0.5 mL/min. Column: Phenomenex Kinetex 2.6μ C18 100A, 50×2.1 mm. Mobile phase A: water with 0.1% formic acid, B: acetonitrile with 0.1% formic acid. Linear gradient: 5-95% B in 3 min followed by 95% B for 1 min. The LC system is equipped with UV and radioactivity (PMT) detectors and coupled to HRMS Agilent 6220 Accurate-Mass TOF LC/MS mass spectrometer (Santa Clara, CA). Autoradiography data was collected on Typhoon FLA 9500 (GE Healthcare Bio-Sciences, Uppsala, Sweden) phosphorimager using FujiFilm Imaging BAS-SR 2025 (Kanagawa, Japan) plates. Human and mice liver microsomes were obtained from BD Gentest (Bedford, MA). C57BL/6 mice were purchased from Harlan Laboratories (Livermore, CA). Animal care followed protocols approved by Genentech's Institutioned Animal Care and Use Committee, which is accredited by the Association for Assessment and Accreditation of Laboratory Animal Care (AAALAC).

Example 1 Synthesis of 1,1-dideutero-2-(1-(benzo[4,5]imidazo[1,2-a]pyrimidine-2-yl)piperidin-4-yl)-1-[$^{18}$F]fluoroethane ([$^{18}$F][A]-d2)

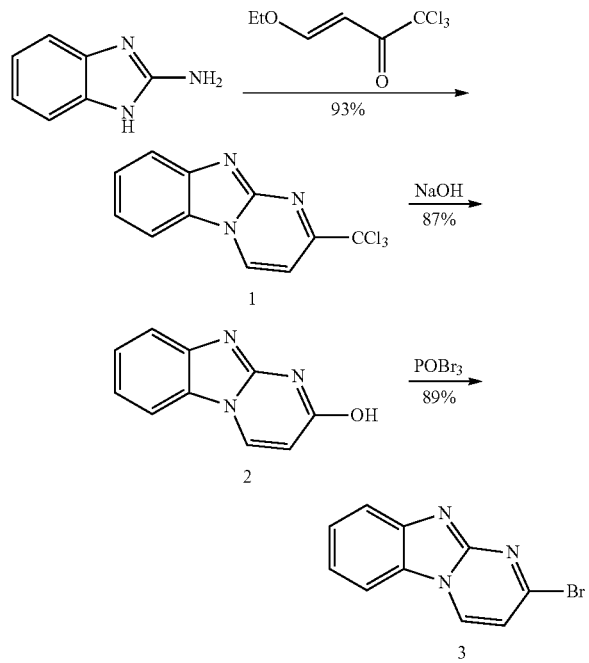

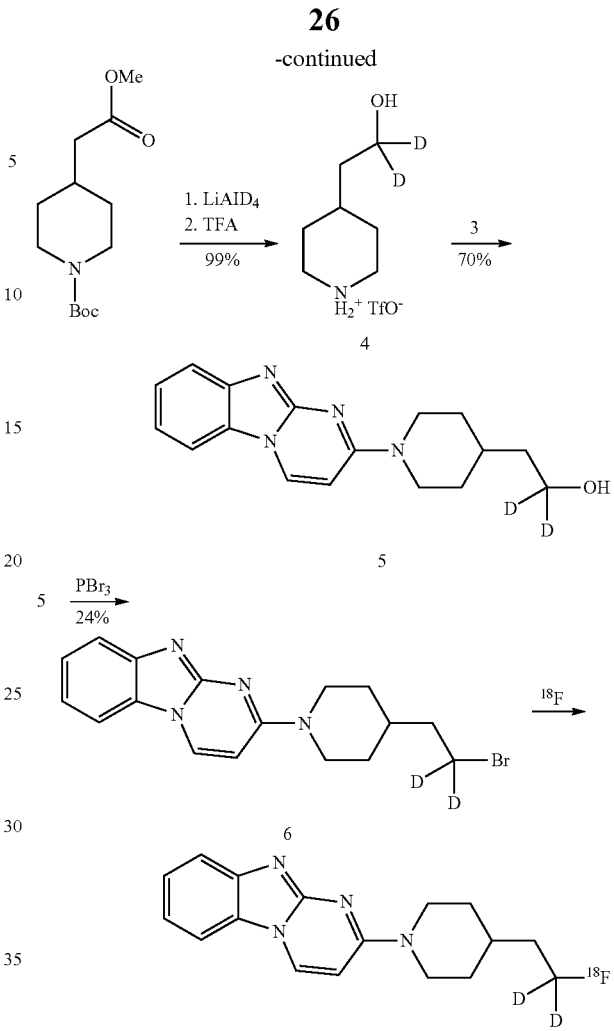

Example 1 - $^{18}$F[A]-d2

$^{18}$F-Fluoride trapped on a Trap-and-Release cartridge was eluted using a solution containing TBHCO₃ (150 μL, 0.075 M) in acetonitrile (500 μL) and water (350 μL). The solvent was evaporated using a gentle stream of nitrogen and microwave heating to 120° C. followed by azeotropic removal of residual water using acetonitrile (4×0.5 mL). The precursor 6 (2 mg) was dissolved in 0.5 mL of acetonitrile and added to a vial containing $^{18}$F-fluoride and heated using a microwave heater to 120° C., 50 W for 350 s. The reaction mixture was concentrated to approximately 100 μL and diluted with water (2 mL) for injection to semi-preparative HPLC (System D). The product was eluted with 15% B for 10 min followed by 20% B for 10-15 min. The fraction containing the product was diluted with water to double the volume and the product was isolated using HLB plus sep-pak cartridge preconditioned with ethanol (10 mL) and water (10 mL), and eluted with ethanol (3 mL). The ethanol was evaporated to dryness and the product [$^{18}$F][A]-d2 was formulated. The radiochemical purity was assessed by LCMS (System E).

Figure 5:
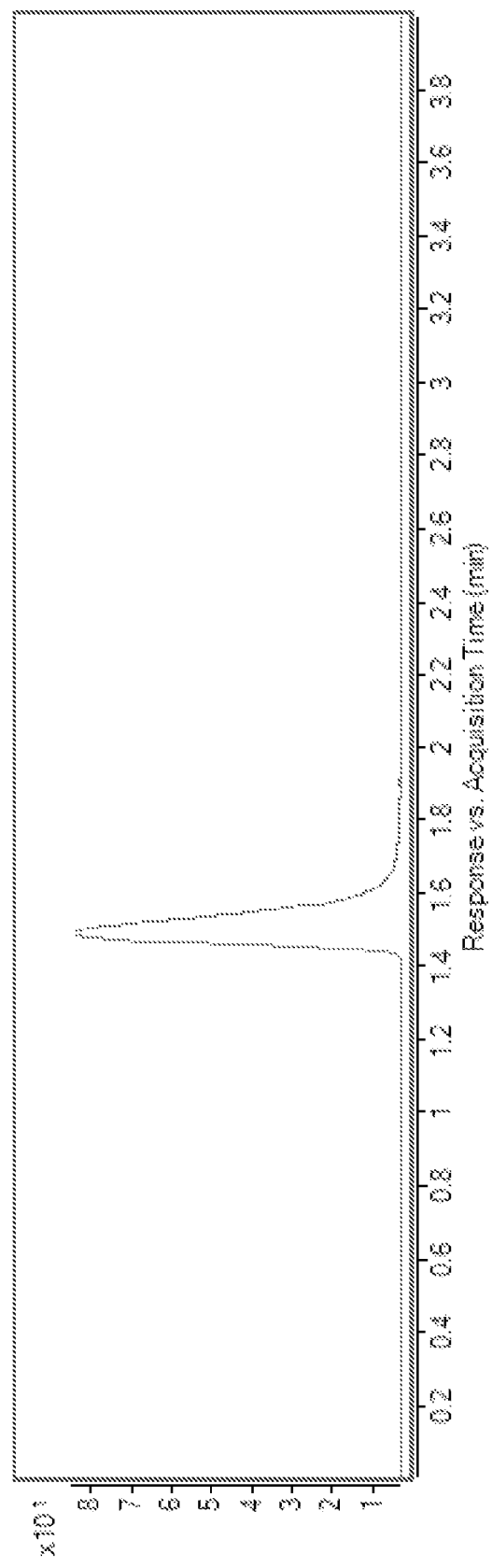
FIG. 5: Radio-HPLC chromatogram of purified [$^{18}$F][A]-d2.

The identity of [$^{18}$F][A]-d2 was confirmed by co-elution with fully characterized cold standard [A]-d2 (System E, retention time 1.5 min). The radiochemical purity of [$^{18}$F][A]-d2 was 99% (FIG. 5) with a specific activity of 70,000-110,000 Ci/mmol.

The intermediate compound 6 was prepared as follows.

a. 2-(trichloromethyl)benzo[4,5]imidazol[1,2-a]pyrimidine (1) 2-Amino-benzimidazole (5.0 g, 37.6 mmol) was suspended in toluene (150 mL) and triethylamine (5.3 mL, 37.6 mmol) was added. (E)-1,1,1-Trichloro-4-ethoxybut-3-en-2-one was added at room temperature. The resulting mixture was heated to 120° C. for 30 minutes. The solvent was evaporated to provide the crude product as yellow solid 10 g (93%). LCMS (System A) m/z found 286.1, calcd for $C_{11}H_7Cl_3N_3$ (M+H)+ 285.96. $^1$H NMR DMSO-d6 δ 9.77 (d, 1H), 8.41 (d, 1H), 7.95 (d, 1H), 7.75 (d, 1H), 7.62 (dd, 1H), 7.53 (dd, 1H).

b. 2-hydroxybenzo[4,5]imidazol[1,2-a]pyrimidine (2) NaOH (49 mL, 1N) was added to compound 1 (10 g, 38 mmol) suspended in acetonitrile (150 mL). The mixture was heated to 90° C. for 2 hours. The mixture was cooled and concentrated to approximately half of the original volume. The mixture was cooled to 0° C. and the pH adjusted to 7-8 using 1N HCl. The precipitate was collected and dried to yield crude compound 2 (6.1 g, 87%). LCMS (System A) m/z found 186.1, calcd for $C_{10}H_8N_3O$ (M+H)+ 186.1. $^1$H NMR DMSO-d6 δ12.60 (bs, 1H), 8.77 (d, 1H), 7.89 (d, 1H), 7.51 (d, 1H), 7.31 (dd, 1H), 7.23 (dd, 1H), 6.10 (d, 1H).

c. 2-bromobenzo[4,5]imidazol[1,2-a]pyrimidine (3) POBr$_3$ (30 g, 106 mmol) was added in portions to a suspension of compound 2 (6.1 g, 33 mmol) in 1,2-dichloroethane (100 mL) and DMF (1 mL) and the mixture was then heated to 100° C. for 1 hour. The reaction mixture was concentrated, poured into iced water (100 mL) and the pH was adjusted to 8 with concentrated NH$_4$OH. The precipitate was collected and washed with iced water and dried in vacuo to yield compound 3 as an brown-orange solid (7.3 g, 89%). LCMS (System A) m/z found 248.1, calcd for $C_{10}H_7BrN_3$ (M+H)+ 247.97. $^1$H NMR DMSO-d6 δ 9.03 (d, 1H), 8.05 (d, 1H), 7.60 (d, 1H), 7.44 (dd, 1H), 7.37 (dd, 1H), 6.42 (d, 1H).

d. 1,1-dideutero-2-(piperidin-4-yl)ethanol (4) Tert-butyl 4-(2-methoxy-2-oxoethyl)piperidine-1-carboxylate (0.5 g, 2 mmol) was dissolved in THF (3 mL) and added drop-wise over 20 min to a suspension of LiAlD$_4$ (0.25 g, 6 mmol) in THF (3 mL) stirred at room temperature. The reaction mixture was stirred for 1 hour then the excess of LiAlD$_4$ was decomposed using water. The precipitation was removed by filtration and washed with THF. The organic extracts were concentrated; the oily residue was dissolved in 98% trifluoroacetic acid and stirred at room temperature for 30 minutes. Trifluoroacetic acid was removed at reduced pressure; the oily residue was triturated with toluene and dried in vacuo. The crude compound 4 was obtained as the trifluoroacetate salt (500 mg, 100%) and used without further purification. LCMS (System A) m/z found 132.06, calcd for $C_7H_{14}D_2NO$ (M+H)+ 132.13. $^1$H NMR DMSO-d6 δ 3.40-3.25 (m, 2H), 2.92-2.82 (m, 2H), 1.92-1.78 (m, 2H), 1.63 (m, 2H), 1.25-1.37 (m, 3H), 8.64-8.30 (bd, 2H), 9.12 (bs, 1H).

e. 1,1-dideutero-2-(1-(benzo[4,5]imidazo[1,2-a]pyrimidine-2-yl)piperidin-4-yl)ethanol (5) A mixture of compound 4 (0.5 g, 2 mmol), diisopropylethylamine (1.4 mL, 8 mmol) and 5 (0.5 g, 2 mmol) in DMF (10 mL) was heated to 95° C. for 2 hours. The reaction mixture was cooled and poured to iced water (100 mL) and the resulting precipitate was collected and dried in vacuo. The mother liquor containing significant amount of product was evaporated to dryness at reduced pressure and the product purified on HPLC (System B, A2 and 5-50% B). Overall 412 mg, (70%) of compound 5 was obtained. LCMS (System A) m/z found 299.3, calcd for $C_{17}H_{19}D_2N_4O$ (M+H)+ 299.18. $^1$H NMR DMSO-d6 δ 8.93 (d, 1H), 7.93 (d, 1H), 7.50 (dd, 1H), 7.31 (dd, 1H), 7.14 (dd, 1H), 6.87 (d, 1H), 4.56 (m, 2H), 4.33 (s, 1H), 3.00 (m, 2H), 1.81-1.75 (m, 3H), 1.39 (d, 2H), 1.19-1.09 (m, 2H).

f. 1,1-dideutero-2-(1-(benzo[4,5]imidazo[1,2-a]pyrimidine-2-yl)piperidin-4-yl)-1-bromoethane (6) A solution of PBr$_3$ (1M, 0.4 mL) in dichloromethane was added slowly to a cooled (0° C.) suspension of compound 5 in dichloromethane. The cooling bath was removed after 10 minutes and the reaction mixture was allowed to warm to room temperature and stirred for 3 hours. The reaction mixture was cooled to 0° C. and an additional portion of PBr$_3$ solution (0.4 mL) was added. The reaction mixture was stirred overnight at room temperature then quenched with few drops of water and concentrated in vacuo. The crude product was purified on HPLC (System B, A2 and 20-60% B) to yield compound 6 (20 mg, 17%) as a white solid. LCMS (System A) m/z found 361.15, calcd for $C_{17}H_{18}D_2BrN_4$ (M+H)+ 361.09. $^1$H NMR DMSO-d6 δ 8.94 (d, 1H), 7.94 (d, 1H), 7.50 (d, 1H), 7.29 (dd, 1H), 7.15 (dd, 1H), 6.88 (d, 1H), 4.48 (m, 2H), 3.04 (m, 2H), 1.95 (m, 1H), 1.83 (m, 4H), 1.19 (m, 2H).

Example 2: Synthesis of 1,1-dideutero-2-(1-(benzo[4,5]imidazo[1,2-a]pyrimidine-2-yl)piperidin-4-yl)-1-fluoroethane ([A]-d2)

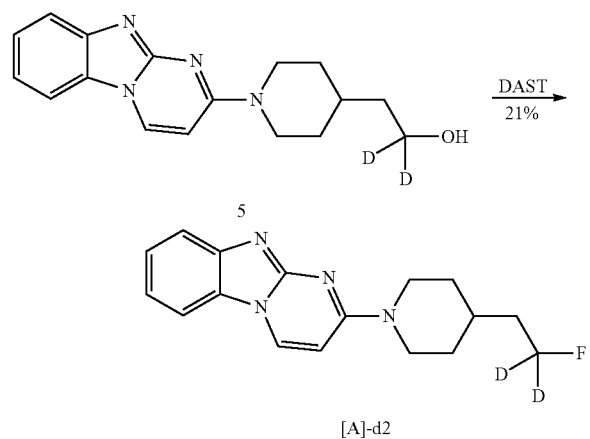

Diethylaminosulfurtrifluoride (0.17 mL, 1.25 mmol) was added to a cooled (−78° C.) solution of compound 5 (75 mg, 0.25 mmol) in dichloromethane (2 mL). The reaction mixture was allowed to warm to room temperature and stirred for 1 hour. The reaction mixture was then cooled to −78° C. and an additional amount of diethylaminosulfur trifluoride (0.17 mL, 1.25 mmol) was added. The reaction mixture was warmed to room temperature and quenched with saturated aqueous solution of NaHCO$_3$. The mixture was concentrated, re-dissolved in DMSO and purified on HPLC (System B, A2 and 5-50% B) to yield compound [A]-d2 as white solid (16 mg, 21%). LCMS (System A) m/z found 301.3 calcd for $C_{17}H_{18}D_2FN_4$ (M+H)+ 301.17. $^1$H NMR DMSO-d6 1H 8.94 (d, 1H), 7.94 (d, 1H), 7.50 (d, 1H), 7.29 (dd, 1H), 7.14 (dd, 1H), 6.88 (d, 1H), 4.57 (m, 2H), 3.01 (m, 2H), 1.84-1.76 (m, 3H), 1.58-1.66 (dd, 2H), 1.15-1.24 (m, 2H); ¹⁹F NMR DMSO-d6 δ-219.1.

Example 3: Synthesis of 2-(1-(benzo[4,5]imidazo[1,2-a]pyrimidine-2-yl)piperidin-4-yl)-1-fluoroethane ([A])

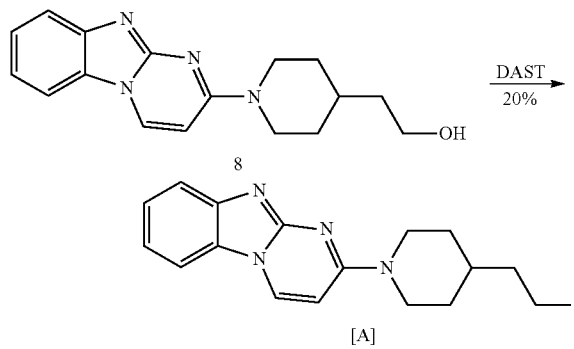

Diethylaminosulfur trifluoride (0.225 mL, 1.7 mmol) was added to a cooled (−78° C.) solution of compound 9 (100 mg, 0.34 mmol) in dichloromethane (2 mL). The reaction mixture was allowed to warm to room temperature and the quenched with saturated aqueous solution of NaHCO₃. The mixture was concentrated, re-dissolved in DMSO and purified on HPLC (System B, A1 and 5-50% B) to yield compound [A] as a white solid (20 mg, 20%). LCMS (System A) m/z found 299.5 calcd for $C_{17}H_{20}FN_4$ (M+H)⁺ 299.16. ¹H NMR DMSO-d6 δ 8.94 (d, 1H), 7.94 (d, 1H), 7.50 (d, 1H), 7.28 (dd, 1H), 7.14 (dd, 1H), 6.88 (d, 1H), 4.62, 4.46 (dt, 2H), 4.60 (bm, 2H), 3.01 (m, 2H), 1.84 (m, 3H), 1.5-1.7 (m, 2H), 1.05-1.3 (m, 2H); ¹⁹F NMR DMSO-d6 δ-217.9.

Example 4: Synthesis of 2-(1-(benzo[4,5]imidazo[1,2-a]pyrimidine-2-yl)piperidin-4-yl)-1-[¹⁸F]fluoroethane ([¹⁸F][A])

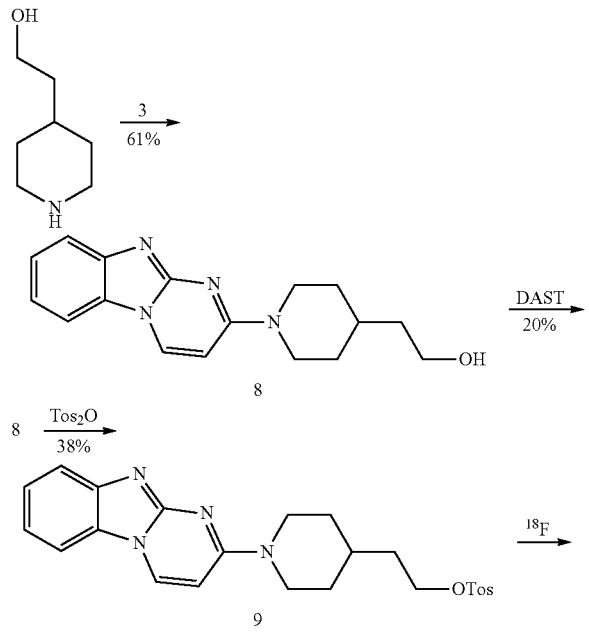

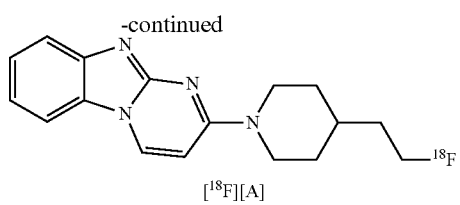

¹⁸F-Fluoride trapped on a Trap-and-Release cartridge was eluted using a solution containing TBHCO₃ (150 μL, 0.075 M) in acetonitrile (500 μL) and water (350 μL). The solvent was evaporated using a gentle stream of nitrogen and microwave heating to 120° C. followed by azeotropic removal of residual water using acetonitrile (4×0.5 mL). Compound 9 (2 mg) was dissolved in 0.5 mL of acetonitrile and added to a vial containing ¹⁸F-fluoride and heated using a microwave heater to 120° C., 50 W for 350 seconds. The reaction mixture was concentrated to approximately 100 μL and diluted with water (2 mL) for injection to semi-preparative HPLC (System D). The product was eluted with 15% B for 10 minutes followed by 20% B for 10-15 minutes. The fraction containing the product was diluted with water to double the volume and the product was isolated using HLB plus sep-pak cartridge preconditioned with ethanol (10 mL) and water (10 mL), and eluted with ethanol (3 mL). The ethanol was evaporated to dryness and the compound [¹⁸F][A] was formulated. The radiochemical purity was assessed by LCMS (System E).

Figure 6:
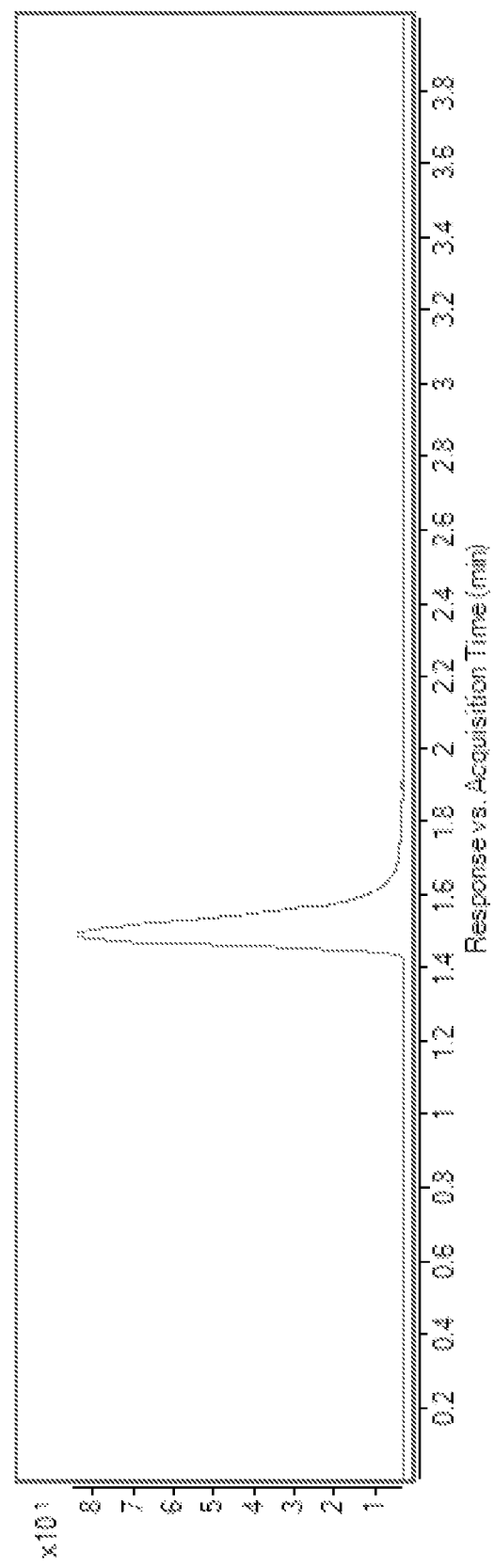
FIG. 6: Radio-HPLC chromatogram of purified [$^{18}$F][A].

The identity of [¹⁸F][A] was confirmed by co-elution with fully characterized cold standard [A] using (System E, retention time 1.5 min). The radiochemical purity of [A] was 99% (FIG. 6) with a specific activity of 70,000-110,000 Ci/mmol.

The intermediate compound 9 was prepared as follows.
a. 2-(1-(benzo[4,5]imidazo[1,2-a]pyrimidine-2-yl)piperidin-4-yl)ethanol (8) 2-(Piperidin-4-yl)ethanol (0.7 g, 5.4 mmol) and compound 3 (1.0 g 4 mmol) were mixed in DMF (12 mL) and the reaction mixture was heated to 100° C. for 30 minutes. The suspension was cooled to room temperature and poured into a 5% aqueous solution of Na₂CO₃ (250 mL). The precipitate was collected, washed with iced water and dried to yield compound 8 as a brown-orange solid (0.74 g, 61%). LCMS (System A) m/z found 297.3 calcd for $C_{17}H_{21}N_4O$ (M+H)⁺ 297.16. ¹H NMR DMSO-d6 δ 9.05 (d, 1H), 8.04 (d, 1H), 7.53 (d, 1H), 7.40 (t, 1H), 7.29 (dd, 1H), 7.09 (d, 1H), 4.59 (m, 2H), 4.37 (bs, 1H), 3.49 (t, 2H), 3.09 (m, 2H), 1.85-1.82 (m, 3H), 1.40 (dt, 2H), 1.17-1.13 (m, 2H).
b. 2-(1-(benzo[4,5]imidazo[1,2-a]pyrimidine-2-yl)piperidin-4-yl)ethyl p-toluenesulfonate (9) A solution of p-toluenesulfonyl anhydride (0.7 g, 2.1 mmol) in pyridine (5 mL) was added to a cooled (0° C.) suspension of compound 8 in pyridine (10 mL). The reaction mixture was allowed to warm to room temperature and stirred for 2 hours. Another portion of p-toluenesufonyl anhydride (0.7 g, 2.1 mmol) was added at room temperature and the mixture was stirred for 30 minutes to complete the reaction. The reaction mixture was poured water (150 mL) and product extracted with dichloromethane (2×50 mL) and the organic extracts were dried over MgSO₄. The crude product was purified on HPLC (System B, A1 and 20-60% B) to yield compound 9 as a p-toluenesulfonate salt (0.29 g, 38%) as a yellowish solid. LCMS (System A) m/z found 451.7, calcd for $C_{24}H_{27}N_4O_3S$ (M+H)⁺ 451.1798; HRMS (System E) m/z found 451.1799. ¹H NMR DMSO-d6 δ 9.15 (d, 1H), 8.13 (d, 1H), 7.82 (d, 2H), 7.57 (d, 1H), 7.52-7.40 (m, 6H), 7.26 (d, 1H), 7.10 (d, 2H), 4.50 (m, 2H), 4.20 t, 2H), 3.11 (m, 2H), 2.44 (s, 3H), 2.28 (s, 3H), 1.70 (m, 3H), 1.6 (m, 2H), 1.06-1.16 (m, 2H).

Example 5 Synthesis of 2-((1R,5S,6s)-6-(2-fluoroethyl)-3-azabicyclo[3.1.0]hexan-3-yl)-(benzo[4,5]imidazo[1,2-a]pyrimidine-2-yl) ([$^{18}$F][B])

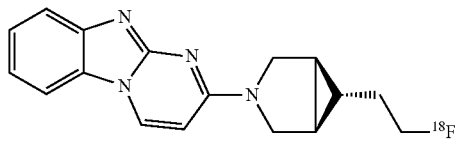

The synthesis of compound C-1 was based on literature protocol. See Example 53 in WO 2004/033451, incorporated herein by reference.

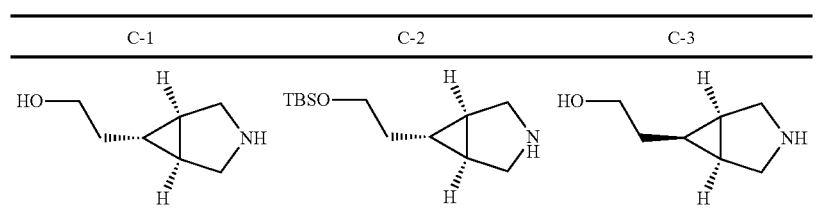

Synthesis of (1S,5R,6s)-6-(2-(tert-butyldimethylsilyloxy)ethyl)-3-azabicyclo[3.1.0]hexane (C-1) and (1R,5S,6s)-6-(2-(tert-butyldimethylsilyloxy)ethyl)-3-azabicyclo[3.1.0]hexane (C-2)

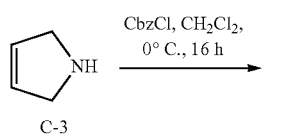

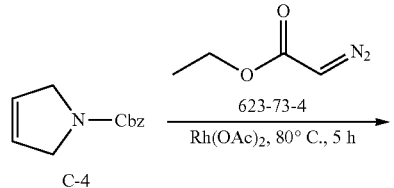

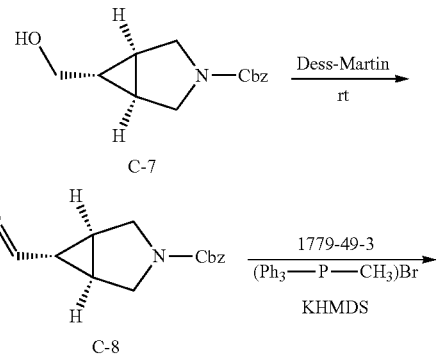

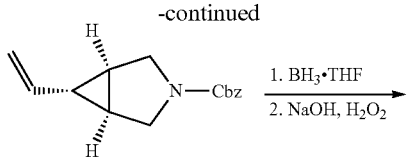

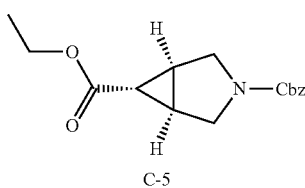

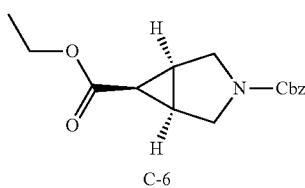

Step 1: benzyl 2,5-dihydro-1H-pyrrole-1-carboxylate (C-4)

Pyrrolidine (C-3) (46.9 g, 672 mmol) was dissolved in DCM (700 mL) at 0° C. Cbz-Cl (95.2 g, 560 mmol) was added slowly. The reaction was allowed to warm room temperature and stirred for 14 hours. The solvent was removed under reduced pressure and the residue was taken up in ethyl acetate. The ethyl acetate solution was washed with 0.5N HCl two times, saturated sodium bicarbonate solution, and brine. It was then dried over MgSO$_4$ and filtered. The filtrate was removed under reduced pressure and the residue was purified by silica-gel column chromatography eluting with 5:1 PE/EA to afford the title compound (46.0 g, 40%) as yellow oil.

MS-ESI: [M+H]$^+$ 204.3

Step 2: 3-benzyl 6-ethyl (1R,5S,6r)-3-azabicyclo$^{3.1.0}$hexane-3,6-dicarboxylate (C-5) and 3-benzyl 6-ethyl (1R,5S,6s)-3-azabicyclo$^{3.1.0}$hexane-3,6-dicarboxylate (C-6)

A solution of ethyl diazoacetate (93 mL) in dichloro ethane (720 mL) was added slowly (over 5 h) to a mixture of benzyl 3-pyrroline1-carboxylate (C-4) (36.0 mg) and rhodium(II) acetate (1.27 g) in dichloroethane (360 mL). The mixture was heated at 80° C. for 5 hrs. The solvent was evaporated under reduced pressure. The residue was taken up in 1:1 Heptane/EA and filtered through neutral alumina. The filtrate was evaporated under reduced pressure and the residue was purified by silica-gel column chromatography eluting with 3:1 Hep/EA (from 3/1 to 2/1) to afford the title compounds: C-5 (18.0 g, 35%) and C-6 (10.0 g, 19%).

MS-ESI: [M+H]$^+$ 290.1

Step 3: (1R,5S,6r)-benzyl 6-(hydroxymethyl)-3-azabicyclo$^{3.1.0}$hexane-3-carboxylate (C-7)

At 0° C. to a solution of 3-benzyl 6-ethyl (1R,5S,6r)-3-azabicyclo$^{3.1.0}$hexane-3,6-dicarboxylate (C-5) (31.8 g, 110 mmol) in THF (110 mL) was added a solution of BH$_3$·THF complex (1M in THF, 275 mL, 275 mmol). The mixture was stirred at 65° C. for 2 hrs. The reaction was allowed to cool to room temperature and the solvent was removed under reduced pressure. Brine and DCM were added and the layers were separated. The aqueous layer was acidified to pH 5 with 1M HCl solution and extracted twice with DCM. The combined organic layer was dried with MgSO$_4$, filtered, and evaporated under reduced pressure. The residue was purified by silica-gel column chromatography eluting with 1:1 PE/EA to afford the title compound (24.0 g, 80%) as colorless oil.

MS-ESI: [M+H]$^+$ 248.1

Step 4: (1R,5S,6r)-benzyl 6-formyl-3-azabicyclo$^{3.1.0}$hexane-3-carboxylate (C-8)

To a solution of (1R,5S,6r)-benzyl 6-(hydroxymethyl)-3-azabicyclo$^{3.1.0}$hexane-3-carboxylate (C-7) (22.2 g, 90 mmol) in dichloromethane (1 L) was added Dess-Martin periodinane (76.32 g, 180 mmol). The mixture was stirred at room temperature for 2 hours and quenched with aqueous Na$_2$S$_2$O$_3$ solution. It was then extracted twice with dichloromethane. The combined extract was washed with brine and saturated NaHCO$_3$ solution. The organic layer was dried over MgSO$_4$, filtered, and evaporated under reduced pressure. The residue was purified by silica-gel column chromatography eluting with 5:1 PE/EA to afford the title compound (19.0 g, 80%) as colorless oil.

MS-ESI: [M+H]$^+$ 246.1

Step 5: (1S,5R,6s)-benzyl 6-vinyl-3-azabicyclo$^{3.1.0}$hexane-3-carboxylate (C-9)

To a suspension of methyltriphenylphosphonium bromide (34.6 g, 97.2 mmol) in THF (80 mL) at 0° C. under N$_2$ atmosphere was added KHMDS (1.0M in THF, 97.2 mL, 97.2 mmol) dropwise. The mixture was allowed to stir at room temperature for 1 hour and then cooled to −78° C. A solution of (1R,5S,6r)-benzyl 6-formyl-3-azabicyclo$^{3.1.0}$hexane-3-carboxylate (C-8) (11.9 g, 48.6 mmol) in dry THF (160 mL) was added slowly. The mixture was warmed to −10° C. and stirred for 1 hour. It was then quenched with saturated NH$_4$Cl solution, extracted twice with ethyl acetate, dried over MgSO$_4$, filtered, and concentrated under reduced pressure. The residue was purified by silica-gel column chromatography eluting with EtOAc/PE (10% to 20) to afford the title compound (8.0 g, 67%).

MS-ESI: [M+H]$^+$ 244.1

Step 6: (1S,5R,6s)-benzyl 6-(2-hydroxyethyl)-3-azabicyclo$^{3.1.0}$hexane-3-carboxylate (C-10)

To a solution of (1S,5R,6s)-benzyl 6-vinyl-3-azabicyclo$^{3.1.0}$hexane-3-carboxylate (C-9) (11.0 g, 45 mmol) in THF (120 ml) cooled at 0° C. was added a solution of BH$_3$·THF complex (1M in THF, 67.5 mL, 67.5 mmol) and the mixture stirred for 30 minutes. The reaction was allowed to warm to room temperature and stirred for 1 hour. It was then re-cooled to 0° C. and treated carefully with 3N NaOH solution (37.5 mL), followed by the addition of H$_2$O$_2$ (30 percent solution, 45 mL). The resulting mixture was warmed to 65° C. and stirred for 2 hours. It was then allowed to cool to room temperature and the solvent was removed in vacuo. Brine and ethyl acetate were added and the layers were separated. The aqueous layer was acidified to pH 5 with 1M HCl solution and extracted twice with ethyl acetate. The combined organic layer was dried over MgSO$_4$, filtered, and concentrated under reduced pressure to afford the crude alcohol, which was used in the next step without further purification.

MS-ESI: [M+H]$^+$ 262.1

Step 7: 2-((1S,5R,6s)-3-azabicyclo$^{3.1.0}$hexan-6-yl) ethanol (C-1)

To a solution of (1S,5R,6s)-benzyl 6-(2-hydroxyethyl)-3-azabicyclo$^{3.1.0}$hexane-3-carboxylate (C-10) (7.44 g, 28.5 mmol) in MeOH (200 mL) was added palladium on carbon (10 percent, 2.23 g). The flask was charged with hydrogen gas and stirred at room temperature for 4 hours. The reaction mixture was then filtered through a pad of Celite and the filtrate was concentrated under reduced pressure to afford the crude title compound, which was purified by mass-guided reverse-phase prep-HPLC to afford the title compound as a yellow oil (2.7 g, 75%).

MS-ESI: [M+H]$^+$ 128.3

$^1$H NMR (500 MHz, CDCl$_3$) δ 4.30 (br s, 2H), 3.70-3.67 (m, 2H), 3.24-3.21 (m, 2H), 3.11-3.08 (m, 2H), 1.53-1.49 (m, 2H), 1.41-1.39 (m, 2H), 0.92-0.90 (m, 1H).

Step 8: (1R,5S,6s)-6-(2-(tert-butyldimethylsilyloxy) ethyl)-3-azabicyclo[3.1.0]hexane (C-2)

At 0° C. to a solution of 2-((1S,5R,6s)-3-azabicyclo [3.1.0]hexan-6-yl)ethanol (C-1) (1.27 g, 10 mmol) in dry DMF (30 mL) was added imidazole (1.7 g, 25 mmol) and tert-butyldimethylsilylchloride (1.95 g, 13 mmol). The mixture was stirred at room temperature for overnight. Ethyl acetate was added and the solution was washed with brine, 1M HCl solution, dried over MgSO$_4$), filtered, and concentrated under reduced pressure. The residue was purified by silica-gel column chromatography eluting with 200:1 ethyl acetate/Et$_3$N to afford the title compound (1.18 g, 49%) as colorless oil.

MS-ESI: [M+H]$^+$ 242.1

$^1$H NMR (500 MHz, DMSO-d$_6$) δ 3.57 (t, J 8.0 Hz, 2H), 2.78-2.76 (m, 2H), 2.62-2.60 (m, 2H), 1.38-1.35 (m, 2H), 1.11-1.09 (m, 2H), 0.86 (s, 9H), 0.61-0.59 (m, 1H), 0.02 (s, 6H).

Synthesis of 2-((1S,5R,6r)-3-azabicyclo[3.1.0]hexan-6-yl)ethanol (D-1)

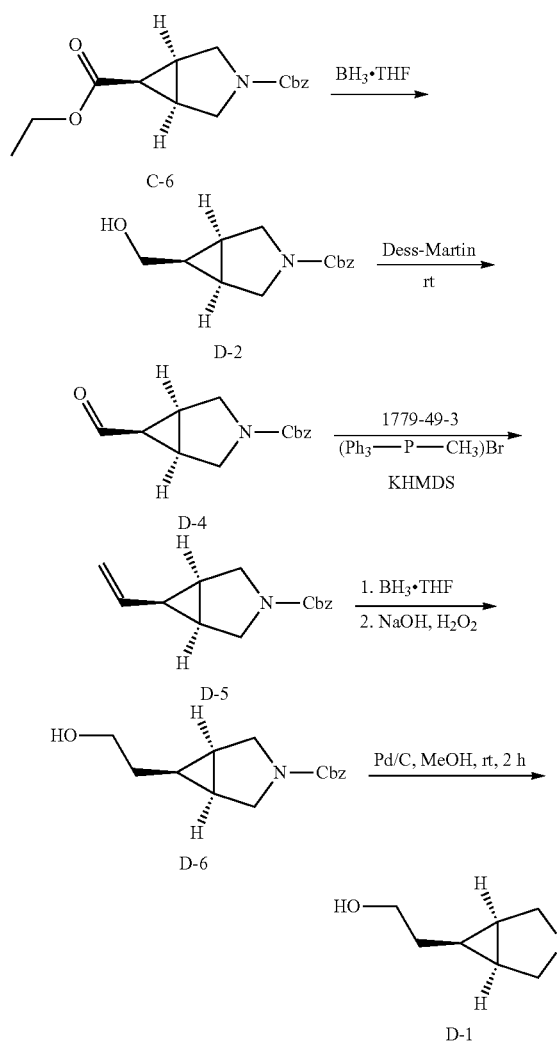

Step 1: (1R,5S,6s)-benzyl 6-(hydroxymethyl)-3-azabicyclo$^{3.1.0}$hexane-3-carboxylate (D-2)

To a solution of (1R,5S,sr)-3-benzyl 6-ethyl 3-aza-bicyclo[3.1.0]hexane-3,6-dicarboxylate (C-6) (10.0 g, 34.6 mmol) in THF (50 mL) at 0° C. was added a solution of BH$_3$·THF complex (1M in THF, 70 mL, 70 mmol). The reaction mixture was stirred at 65° C. for 2 hrs. The reaction was allowed to cool to room temperature and the solvent was removed under reduced pressure. To the residue was added brine and DCM. The layers of the resulting mixture was separated. The aqueous layer was acidified to pH 5 with 1M HCl solution and extracted twice with DCM. The combined organic extract was dried with MgSO$_4$, filtered, and evaporated under reduced pressure. The residue was purified by silica-gel column chromatography eluting with 1:1 PE/EA to afford the title compound (6.4 g, 75%) as colorless oil.

MS-ESI: [M+H]$^+$ 248.1

Step 2: (1R,5S,6s)-benzyl 6-formyl-3-azabicyclo[3.1.0]hexane-3-carboxylate (D-4)

To a solution of (1R,5S,6s)-benzyl 6-(hydroxymethyl)-3-azabicyclo[3.1.0]hexane-3-carboxylate (D-2) (11.1 g, 45 mmol) in dichloromethane (0.5 L) was add Dess-Martin periodinane (38.2 g, 90 mmol). The mixture was stirred at room temperature for 2 hours. The reaction was quenched with aqueous Na$_2$S$_2$O$_3$ solution, extracted twice with dichloromethane. The combined extract was washed with brine and saturated NaHCO$_3$ solution, dried over MgSO$_4$, filtered, and evaporated under reduced pressure. The residue was purified by silica-gel column chromatography eluting with 5:1 PE/EA to afford the title compound (9.0 g, 76%) as colorless oil.

MS-ESI [M+H]$^+$ 246.1

Step 3: (1S,5R,6r)-benzyl 6-vinyl-3-azabicyclo[3.1.0]hexane-3-carboxylate (D-5)

To a suspension of methyltriphenylphosphonium bromide (23.1 g, 65 mmol) in THF (60 mL) at 0° C. under N$_2$ atmosphere was added [KHMDS] (1.0M in THF, 65 mL, 65 mmol) dropwise. The mixture was allowed to stir at room temperature for 1 hour and then cooled to −78° C. A solution of (1R,5S,6s)-benzyl 6-formyl-3-azabicyclo[3.1.0]hexane-3-carboxylate (D-4) (8.0 g, 32.4 mmol) in anhydrous THF (100 mL) was added slowly and the mixture was warmed to −10° C. and stirred for 1 hour. The reaction was quenched with saturated NH$_4$C$_1$ solution and evaporated under reduced pressure. The residue was extracted twice with ethyl acetate, dried over MgSO$_4$, filtered, and concentrated under reduced pressure. The residue was purified by silica-gel column chromatography eluting with EtOAc/hexanes (10% to 20%) to afford the title compound (5.3 g, 66%).

MS-ESI: [M+H]$^+$ 244.1

Step 4: (1S,5R,6r)-benzyl 6-(2-hydroxyethyl)-3-azabicyclo[3.1.0]hexane-3-carboxylate (D-6)

To a solution of (1S,5R,6r)-benzyl 6-vinyl-3-azabicyclo[3.1.0]hexane-3-carboxylate (D-5) (5.3 g, 21.7 mmol) in THF (60 mL) cooled at 0° C. was added a solution of BH$_3$·THF complex (1M in THF, 32.5 mL, 32.5 mmol). The mixture stirred for 30 minutes. The reaction was allowed to warm to room temperature and stirred for 1 hour. It was then re-cooled to 0° C. The mixture was treated carefully with 3N NaOH solution (18.1 mL), followed by the addition of H$_2$O$_2$ (30 percent solution, 22 mL). The resulting mixture was stirred at 65° C. for 2 hours. The reaction was allowed to cool to room temperature and the solvent was removed under reduced pressure. To the residue was added brine and athyl acetate. The layers of the resulting mixture were separated. The aqueous layer was acidified with 1M HCl solution to pH 5, extracted twice with ethyl acetate, dried over MgSO$_4$, filtered, and concentrated under reduced pressure to afford the crude title compound, which was used in the next step without further purification.

MS-ESI: [M+H]+ 262.1

Step 5: 2-((1S,5R,6r)-3-azabicyclo[3.1.0]hexan-6-yl)ethanol (D-1)

To a solution of (1S,5R,6r)-benzyl 6-(2-hydroxyethyl)-3-azabicyclo[3.1.0]hexane-3-carboxylate (D-6) (3.72 g, 14.25 mmol) in MeOH (100 mL) was added palladium on carbon (10 percent, 1.13 g). The flask was charged with hydrogen gas and stirred at room temperature for 4 hours. The reaction mixture was then filtered through a pad of celite. The filtrate was concentrated under reduced pressure to afford the crude title compound, which was purified by mass-guided reverse-phase prep-HPLC to afford the target compound as which solid.

MS-ESI: [M+H]+ 128.3

$^1$H NMR (500 MHz, DMSO-d$_6$) δ 5.8-5.0 (br s, 2H), 3.47-3.43 (m, 2H), 3.38-3.36 (m, 1H), 3.23-3.21 (m, 1H), 3.00-2.98 (m, 1H), 2.82-2.79 (m, 1H), 1.55-1.53 (m, 1H), 1.48-1.45 (m, 2H), 1.28-1.24 (m, 1H), 0.88-0.79 (m, 1H).

The compounds B-2, B-3, and B-4 were synthesized using procedures similar to those above with following yields and analytical data.

Compound B-2 Yellow solid, yield 80-90%. LCMS 295.25 @0.82 min>99%. NMR DMSO-d6 400 MHz 9.06 (d, 1H), 8.06 (d, 1H), 7.54 (d, 1H), 7.42 (t, 1H), 7.31 (t, 1H), 6.73 (d, 1H), 4.47 (bs, 1H), 3.87 (dd, 2H), 3.66 (m, 2H), 3.48 (t, 2H), 1.60 (m, 2H), 1.43 (dq, 2H), 0.63 (m, 1H) Compound B-3 (cold standard) White solid, yield 26%. LCMS 297.59 @0.87 min>99%. NMR 300 MHz DMSO-d6 1H 8.95 (d, 1H), 7.95 (d, 1H), 7.50 (d, 1H), 7.30 (dt, 1H), 7.17 (dt, 1H), 6.54 (d, 1H), 4.59, 4.43 (dt, 2H), 3.7-4.0 (m, 2H), 3.5-3.7 (m, 2H), 1.55-1.8 (m, 4H), 0.64 (m, 1H). 19F -216.62

Compound B-4 (precursor) White solid, yield 75%. LCMS: 357.26 359.25 @1.03 min>99%. NMR 400 MHz DMSO-d4 8.94 (d, 1H), 7.93 (d, 1H), 7.50 (d, 1H), 7.29 (dd, 1H), 7.14 (dd, 1H), 6.51 (d, 1H), 3.90-3.80 (m, 2H), 3.59 (t, 2H), 3.50-3.70 (m, 2H), 1.83 (dd, 2H), 1.67 (m, 2H), 0.71 (m, 1H)

[18F][B] can be prepared under the similar labeling conditions as described above with a decay corrected yield of 5-10%.

Prophetic Synthesis of [$^{18}$F][B]-d2

Oxidation of amino alcohol to amino acid C-1

H$_2$IO$_6$ (85 mg) is suspended in water (1 mL) and acetonitrile (1 mL) and stirred vigorously for 15 min. Amino alcohol (50 mg) is added followed by the addition of pyridinium chlorochromate (5 mg). The reaction mixture is stirred for 2 h at the room temperature and the final product isolated.

Method for Boc protection of amino acid 2-1

To a solution of Compound C-1 in DCM the tert-butyloxycarbonyl anhydride (1.5 eq) and DIEA (3 eq) are added at 0° C. The mixture is allowed to warm to room temperature and stirred until complete conversion.

Synthesis of methyl ester 3-1

Freshly prepared solution of diazomethane in ether (Diazald kit) is added to a solution of Compound 2-2 in dioxane at room temperature. The reaction is monitored and additional diazomethane solution is added to complete the conversion of Compound 2-2 to methylester.

Synthesis of dideutero amino alcohol 4-1

The methylester (Compound 3-1) is reduced with LiAlD$_4$ to deuterated alcohol and deprotected with TFA to provide Compound 4-1 as described above.

The remaining steps track those shown for [$^{18}$F][A]-d2.

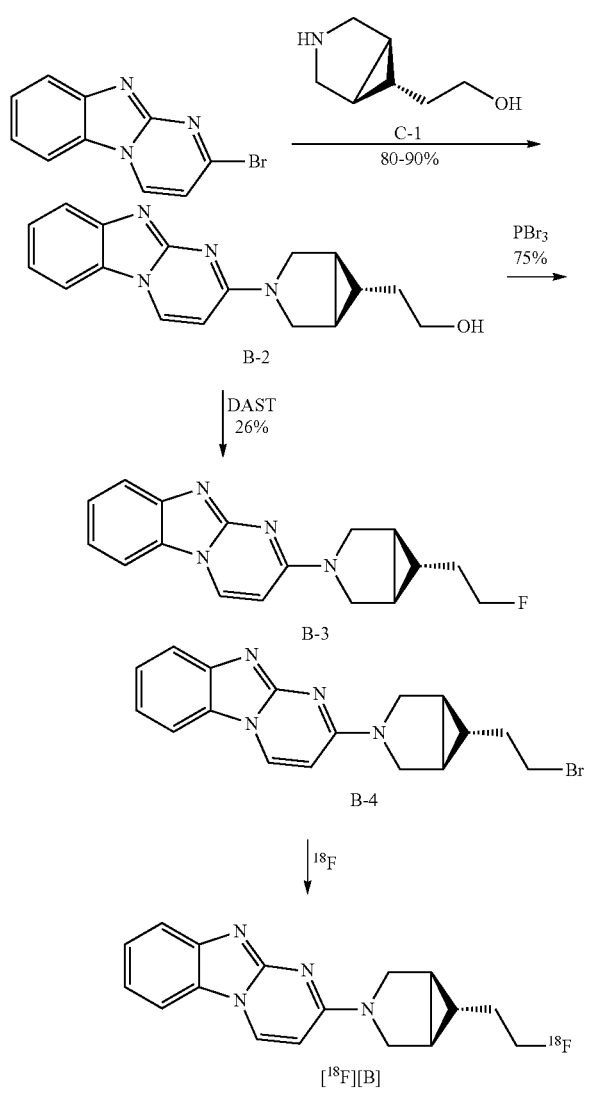

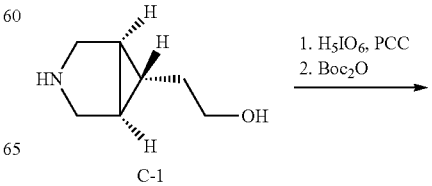

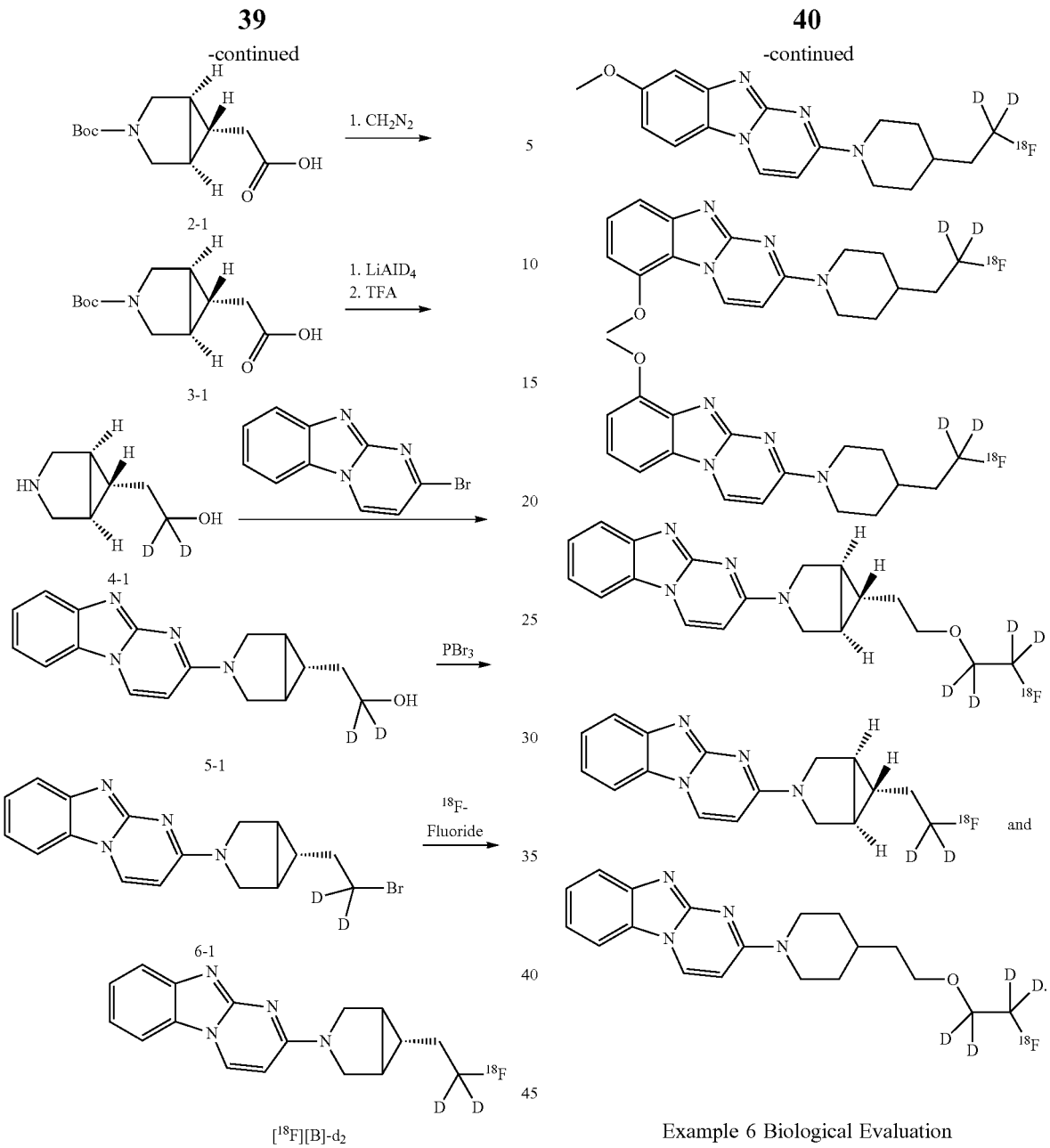

Synthesis of Additional Compounds

Using procedures similar to those described herein, the following compounds of formula (I) can also be prepared:

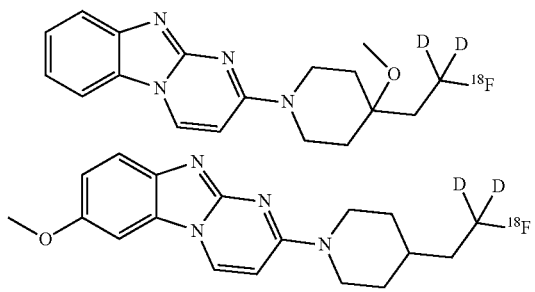

Example 6 Biological Evaluation

Autoradiography The tracer [$^{18}$F][A] or [$^{18}$F][A]-d2 was dissolved in PBS containing 5% DMSO and 5% ethanol at final concentration 40 μCi/mL. Then 0.5 ml of stock solution was transferred to a microscope slide with 5 μm thick freshly dried section of a tissue and incubated for 90 min at room temperature. The slides were washed by dipping into following solutions: PBS for 1 min, 70% ethanol 2 min, 30% ethanol 2 min and PBS 1 min. The samples were dried at room temperature for 30 min and exposed to phosphorimager plate for 20 h. The exposed plates were scanned at 25 μm resolution.

MicroPET Imaging The PET imaging was performed on Inveon PET/CT scanner (Siemens Medical Solutions USA Inc.). Animals anesthetized with sevoflurane were placed head-first, prone position on the scanner bed and dynamic 45 min scans were initiated. Approximately 3.7 MBq of $^{18}$F-radiolabeled tracer in isotonic solution (100-130 μL) was administered as 60 second intravenous infusion via the tail vein. Body temperature was measured by a rectal probe and maintained with warm air flow at 37° C. Full-body iterative image reconstructions were obtained using maximum a posteriori algorithm (MAP, hyperparameter β 0.05) and corrected for signal attenuation using the tissue density obtained from CT. Projections were created with PMOD 3.305 (PMOD Technologies, Ltd., Zurich, Switzerland) and used to obtain quantitative activity levels in each organ of interest using region-of-interest analysis.

Microsomal stability assays The tracer [$^{18}$F][A]-d2 or [$^{18}$F][A] was dissolved in potassium phosphate (Kpi) buffer (100 mM) at concentration 500-600 µCi/mL. The non-radioactive 7 and 10 were dissolved in Kpi buffer at 10 µM concentration. The reaction vessel was charged with human or mouse liver microsome suspension (12.5 µL, 20 mg/mL) followed by Kpi buffer (388 µL, 10 mM), NADPH (50 µL, 10 mM) and incubated at 37° C. for 5-10 min. A solution of the radioactive [$^{18}$F][A]-d2 or [$^{18}$F][A] (50 µL, 250-300 µCi) or non-radioactive 7 or 8 (50 µL, 10 µM) were added to the reaction vessel and the mixture was incubated at 37° C. Aliquots (50 µL) of the reaction mixture were taken at 5, 15 and 45 minutes post addition of the tested compound, mixed with ice-cold acetonitrile (100 µL) and centrifuged. The supernatant was analyzed by LCMS (System E).

Statistical analysis The statistical analysis was performed and the plots were constructed with R software version 2.10.1 (R Foundation for Statistical Computing, Vienna, Austria). Statistical significance was determined using Student's t-test and p of less than 0.05 was considered significant. All data are presented as mean±standard deviation.

Results and Discussions

Both [$^{18}$F][A] and [$^{18}$F][A]-d2 were prepared in a single step using in-situ generated [$^{18}$F]TBAF. After HPLC purification, [$^{18}$F][A]-d2 was obtained in 7% decay corrected radiochemical yield within 90 minutes (n=4); [$^{18}$F][A] was prepared in 12% yield within 96 min (n=9). The radiochemical purity of both tracers was greater than 99% and specific activity in the range of 70-110 Ci/µmol.

Autoradiographic evaluation of [$^{18}$F][A] and [$^{18}$F][A]-d2 was performed using brain tissues collected postmortem from human donors. Both compounds, [$^{18}$F][A] and [$^{18}$F][A]-d2, showed identical tau specific binding patterns (FIG. 1). The positive staining was found in grey matter of tissues containing high level of NFTs and high AD-amyloid characterized as Braak score 5. The negative control tissues containing high or moderate AD-amyloid burden but no NFTs with Braak score 3 or 2 were not positively stained with either [$^{18}$F][A] or [$^{18}$F][A]-d2. The NFT and Aβ-amyloid burden was measured by standard immunohistochemical methods.

Figure 3A:
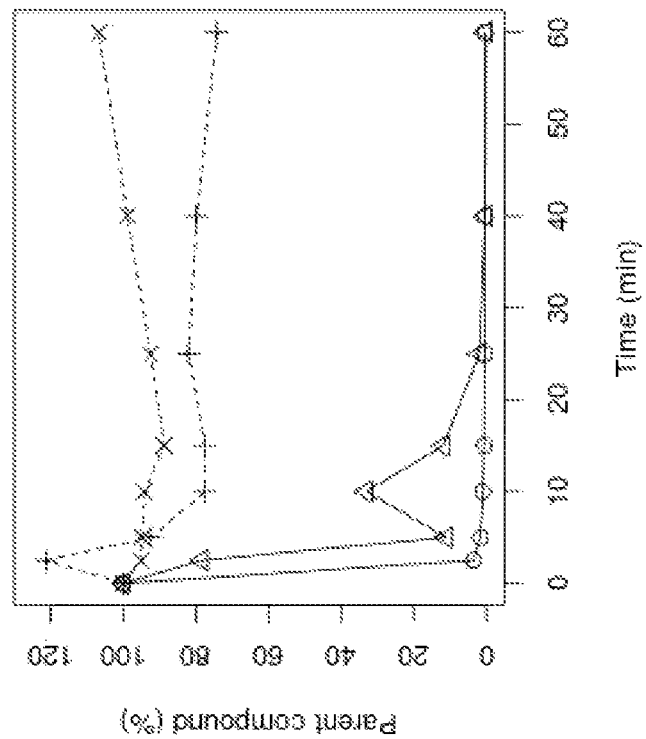
FIGS. 3A-3B: Human and mouse liver microsome assay performed with non-radiolabeled [A] and [A]-d2 showed higher stability of [A]-d2 and slower metabolism of both compounds in presence of human liver microsomes.
Figure 3B:
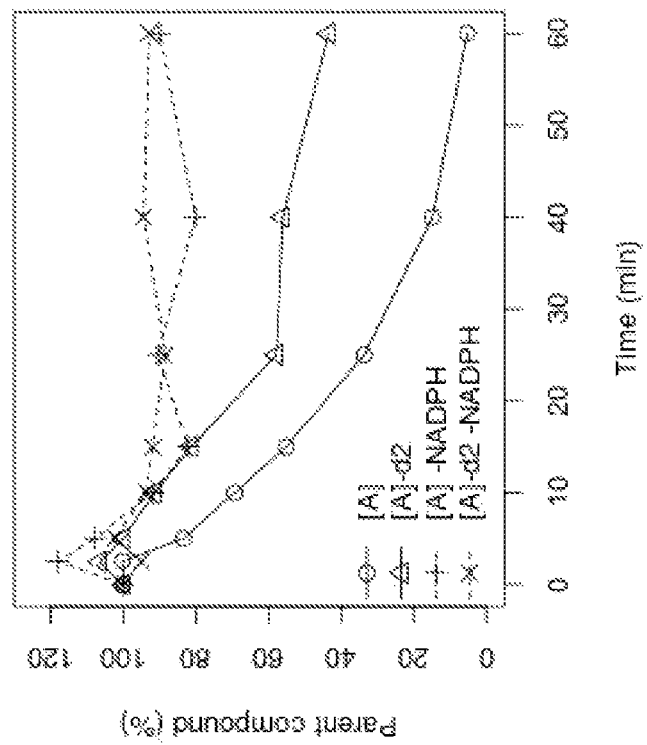

The metabolic stability and [$^{18}$F]F$^-$ formation was assessed in vitro using human and mice liver microsomes (Tipre, D. N, et al., *J. Nucl. Med.* 2006 47 (2), 345-53). Slower metabolism of [A] in human than in mouse liver microsome assay was reported, in both species, the metabolism of [A] was NADPH dependent indicating possible involvement of cytochrome P450 enzymes (Zhang, W., et al., *J. Alzheimer's Disease:JAD* 2012 31 (3), 601-12). A comparison of non-radiolabeled [A] and [A]-d2 in liver microsome assay revealed a higher stability of [A]-d2 compared to [A] in both human and mouse liver microsomes. The metabolism of [A] and [A]-d2 in mouse liver microsomes was very rapid, the fraction of unmetabolized [A] decreased to 2% at 5 min but the amount of [A]-d2 was 11% (FIG. 3B) In human liver microsomes, the amount of remaining [A] was 15% at 40 min but [A]-d2 amount was still 56% (FIG. 3A). The metabolism of both [A] and [A]-d2 was NADPH dependent suggesting the involvement of cytochrome P450 enzymes.

Figure 2A:
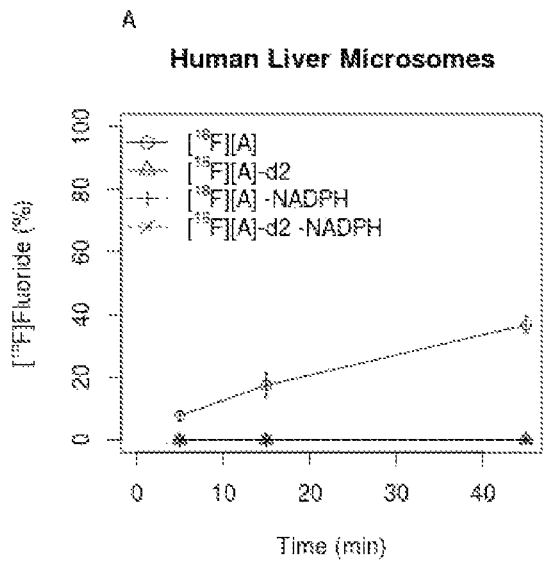
FIGS. 2A-2D: In vitro assessment of metabolic stability of [$^{18}$F][A]-d2 and [$^{18}$F][A] using mouse and human liver microsomes. The formation of [$^{18}$F]fluoride (2A and 2B) and amount of remaining parent compound were measured (2C and 2D) at 5, 15 and 45 min.
Figure 2B:
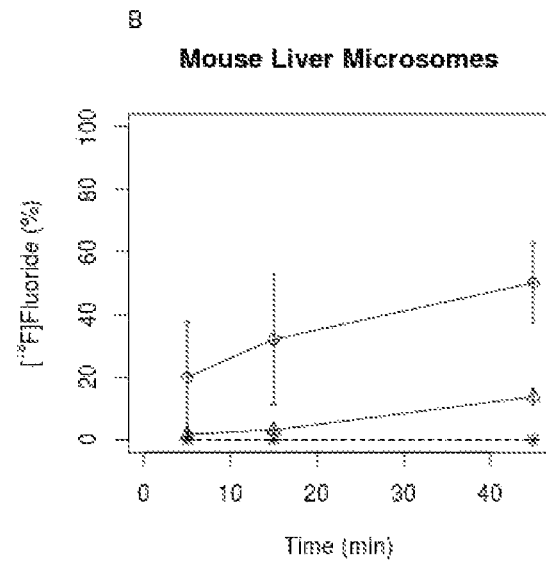
Figure 2C:
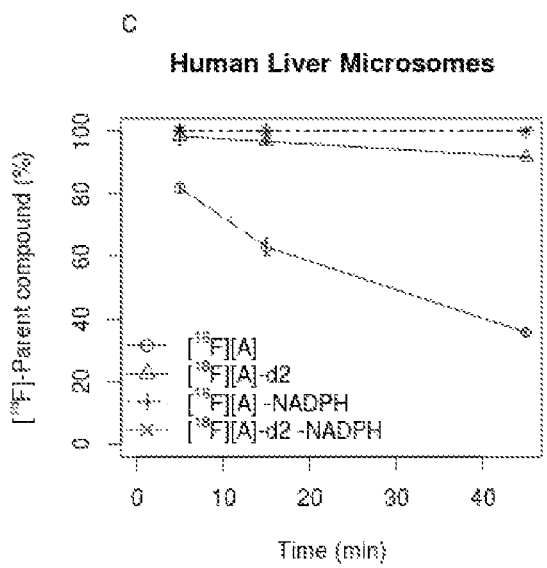
Figure 2D:
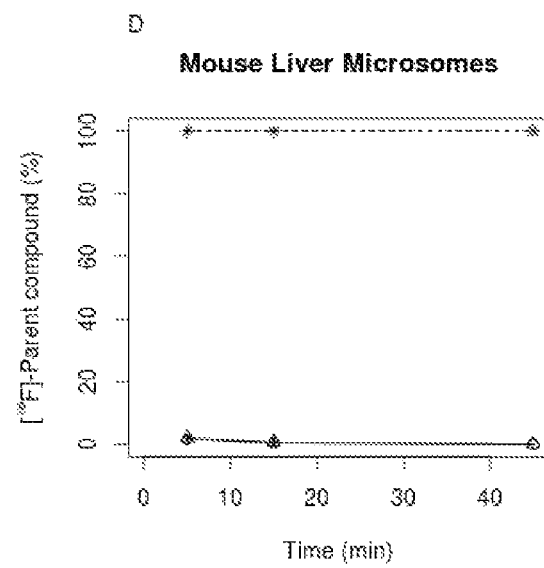

The radiolabeled tracers [$^{18}$F][A] and [$^{18}$F][A]-d2 (n=3) were also incubated with human or mouse liver microsome suspensions with or without NADPH at 37° C. and the mixture was analyzed for a presence of radioactive metabolites at 5, 15 and 45 min (FIG. 2A-2D). In the presence of mouse liver microsomes, both the [$^{18}$F][A] and [$^{18}$F][A]-d2 metabolized rapidly to $^{18}$F-fluoride (retention time (rt)=0.38 min), and two radioactive metabolites M2 and M1 (rt=1.2 and 1.4 min). The conversion of [$^{18}$F][A] and [$^{18}$F][A]-d2 to M2 and M1 was very fast and the amount of parent compound (rt=1.5 min) was only 1.6±0.9% and 2.0±0.3 respectively (FIG. 2D) at 5 minutes. At 45 minutes, the amount of [$^{18}$F]F$^-$ formed from [$^{18}$F][A] (50.1±12.9%) was significantly (p=0.035) larger compared to the amount of [$^{18}$F]F$^-$ formed from [$^{18}$F][A]-d2 (13.8±2.4%) (FIG. 2B). In the presence of human liver microsomes, the conversion of both tracers to [$^{18}$F]F$^-$, M1 and M2 was slower than in mouse liver microsomes. Nevertheless, [$^{18}$F][A] was still metabolized more rapidly than dideuterated [$^{18}$F][A]-d2. After 45 min incubation with human liver microsomes, the fraction attributed to parent compound ([$^{18}$F][A]) was 35.7±0.9% and the fraction of radioactivity attributed to [$^{18}$F][A]-d2 was 91.7±0.21% (FIG. 2C). The amount of [$^{18}$F]F$^-$ was 36.7±2.7% in case of [$^{18}$F][A] but no [$^{18}$F]F$^-$ was detected as a product of [$^{18}$F][A]-d2 metabolism in human liver microsomes at 45 minutes (FIG. 2A).

Figure 4D:
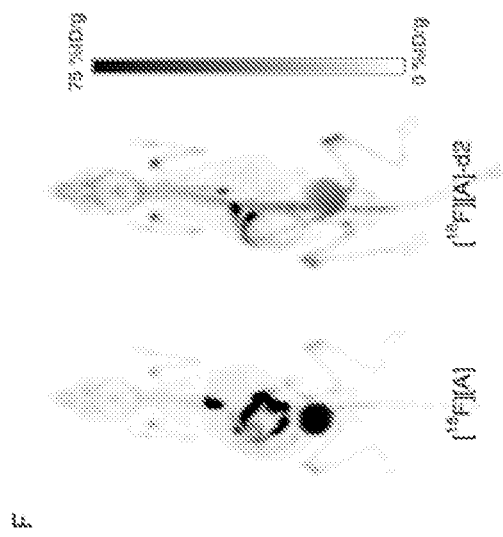
Figure 4E:
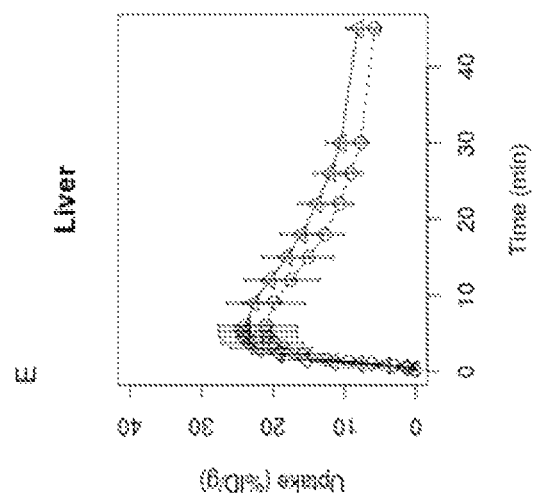
Figure 4F:
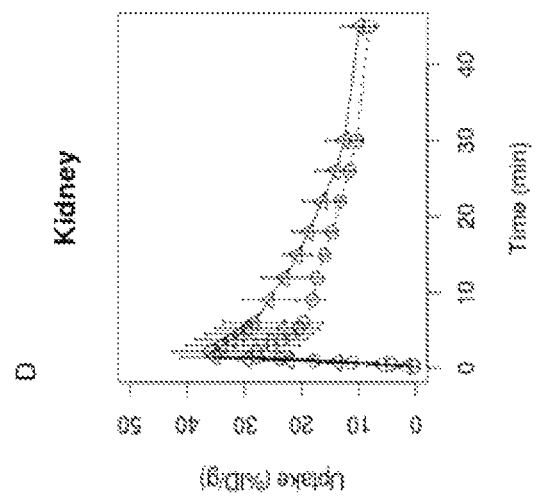

Dynamic PET imaging in mice (n=6) was used to assess in vivo properties of [$^{18}$F][A] and [$^{18}$F][A]-d2. The uptake of both tracers was indistinguishable in liver and kidneys (FIG. 4E, 4D). The peak uptakes in brain (8.3±2.0 and 7.4±2.2% ID/g) were not significantly different between the tracers (p=0.444) (FIG. 4C) as well as the blood signal obtained from whole heart (FIG. 4B). However, the mice injected with [$^{18}$F][A]-d2 showed significantly (p=1.19×10$^{-4}$) reduced bone uptake (14.3±1.7% ID/g) at 30-45 min post tracer injection compared to the bone uptake of mice injected with [A] (31.2±4.8% ID/g) as a consequence of slower enzymatic defluorination (FIG. 4A). The maximum intensity projections (FIG. 4F) illustrate the improvements in image quality. The PET imaging data is in excellent agreement with results of the comparison of [$^{18}$F][A] and [$^{18}$F][A]-d2 in vitro using mouse liver microsomes. In the in vitro experiment the substitution of geminal hydrogens in [$^{18}$F][A] with deuterium caused 73% reduction in [$^{18}$F]F$^-$ formation and the reduction in bone uptake observed by in vivo PET is also close to 54%.

The in vitro and in vivo comparison of [$^{18}$F][A]-d2 and [$^{18}$F][A] suggests that [$^{18}$F][A]-d2 is more metabolically stable leading to significantly less [$^{18}$F]F$^-$ formation than [$^{18}$F][A]. The data also demonstrate that the [A]-d2 metabolism and formation of [$^{18}$F]F$^-$ in human is expected to be much lower than in mouse, hence the [$^{18}$F][A]-d2 could provide tau-specific images with significantly lower background than [$^{18}$F][A] in clinical setting.

Further Studies

The radiolabeled tracers [$^{18}$F][A] and [$^{18}$F][A]-d2 (n=3) were incubated with human, rhesus or mouse liver microsome suspension with or without NADPH at 37° C. and the mixture was analyzed for a presence of radioactive metabolites at 5, 15 and 45 min. In the presence of mouse and rhesus liver microsomes, both the [$^{18}$F][A] and [$^{18}$F][A]-d2 metabolized rapidly to $^{18}$F-fluoride (retention time (rt)=0.38 min), and two radioactive metabolites M2 and M1 (rt=1.2 and 1.4 min). The conversion of [$^{18}$F][A] and [$^{18}$F]

Figures 7A, 7B, 7C, 7D, 7E, 7F:
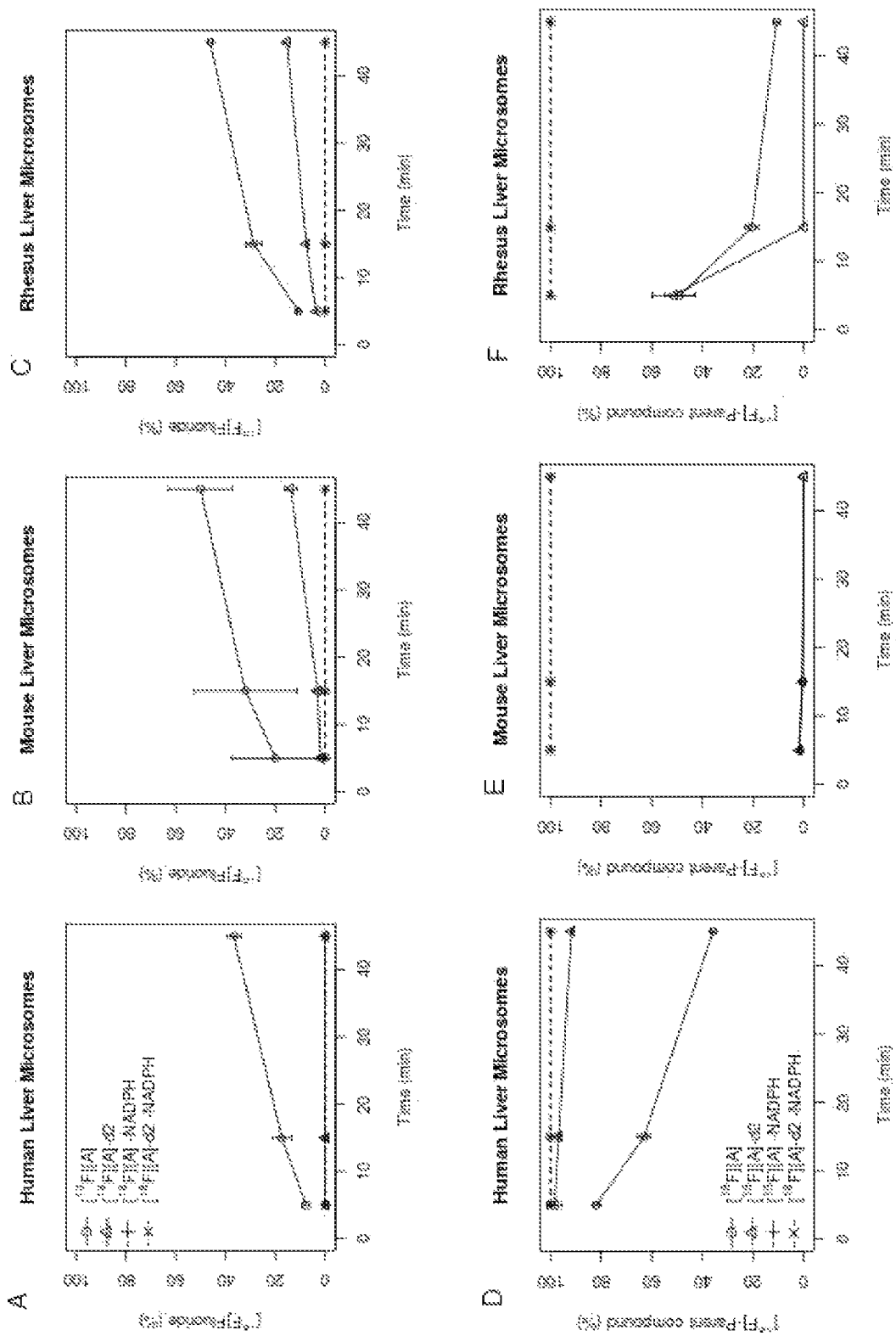
FIGS. 7A-7F: In vitro assessment of metabolic stability of [$^{18}$F][A]-d2 and [$^{18}$F][A] (n=3) using human, rhesus or mouse liver microsomes. The formation of [$^{18}$F]fluoride (7A-7C) and amount of remaining parent compound were measured (7D-7F) at 5, 15 and 45 min.

[A]-d2 to M2 and M1 was very fast and the amount of parent compound (rt=1.5 min) was only 1.6±0.9% and 2.0±0.3 respectively at 5 min (FIG. 7E) in presence of mouse liver microsomes. Both compounds were slightly more stable in rhesus liver microsomes (FIG. 7F). At 45 min, the amount of [$^{18}$F]F$^-$ formed from [$^{18}$F][A](50.1±12.9%) was significantly (p=0.035) larger than the amount of [$^{18}$F]F$^-$ formed from [$^{18}$F][A]-d2 (13.8±2.4%) in mouse liver microsomes (FIG. 7B) and a similar effect was observed in rhesus liver microsomes ([$^{18}$F][A]-d2: 15.4±1.3% vs. [$^{18}$F][A]: 46.1±1.0%) (FIG. 7C). In the presence of human liver microsomes, the conversion of both tracers to [$^{18}$F]F$^-$, M1 and M2 was slower than in mouse or rhesus liver microsomes. Nevertheless, [$^{18}$F][A] was still metabolized more rapidly than dideuterated [$^{18}$F][A]-d2. After 45 min incubation with human liver microsomes, the fraction attributed to parent compound ([$^{18}$F][A]) was 35.7±0.9% and the fraction of radioactivity attributed to [$^{18}$F][A]-d2 was significantly higher 67.1±6.3% (p=0.012) (FIG. 7D). The amount of [$^{18}$F]F$^-$ was 36.7±2.7% in case of [$^{18}$F][A] but no [$^{18}$F]F$^-$ was detected (p=0.002) as a product of [$^{18}$F][A]-d2 metabolism in human liver microsomes at 45 min (FIG. 7A).

The microsomal stability assessment as a predictor of in-vivo stability of [$^{18}$F][A] and [$^{18}$F][A]-d2 suggests significantly higher metabolic stability of [$^{18}$F][A]-d2 compared to [$^{18}$F][A] and significantly slower rate of $^{18}$F-fluoride formation in rhesus and mice. Unexpectedly, $^{18}$F-fluoride was not detected as a metabolite of [$^{18}$F][A]-d2 using human liver microsomes at all, suggesting much greater stability of [$^{18}$F][A]-d2 in human than in rhesus or mice.

These PET images acquired in mice and rhesus using [$^{18}$F][A] and [$^{18}$F][A]-d2 further confirmed the in-vitro prediction of lower $^{18}$F-fluoride formation seen as an uptake of radioactivity in mineral bone in case of [$^{18}$F][A]-d2 compared to [$^{18}$F][A].

Administration of [$^{18}$F][A]-d2 in Primates

Figure 8A:
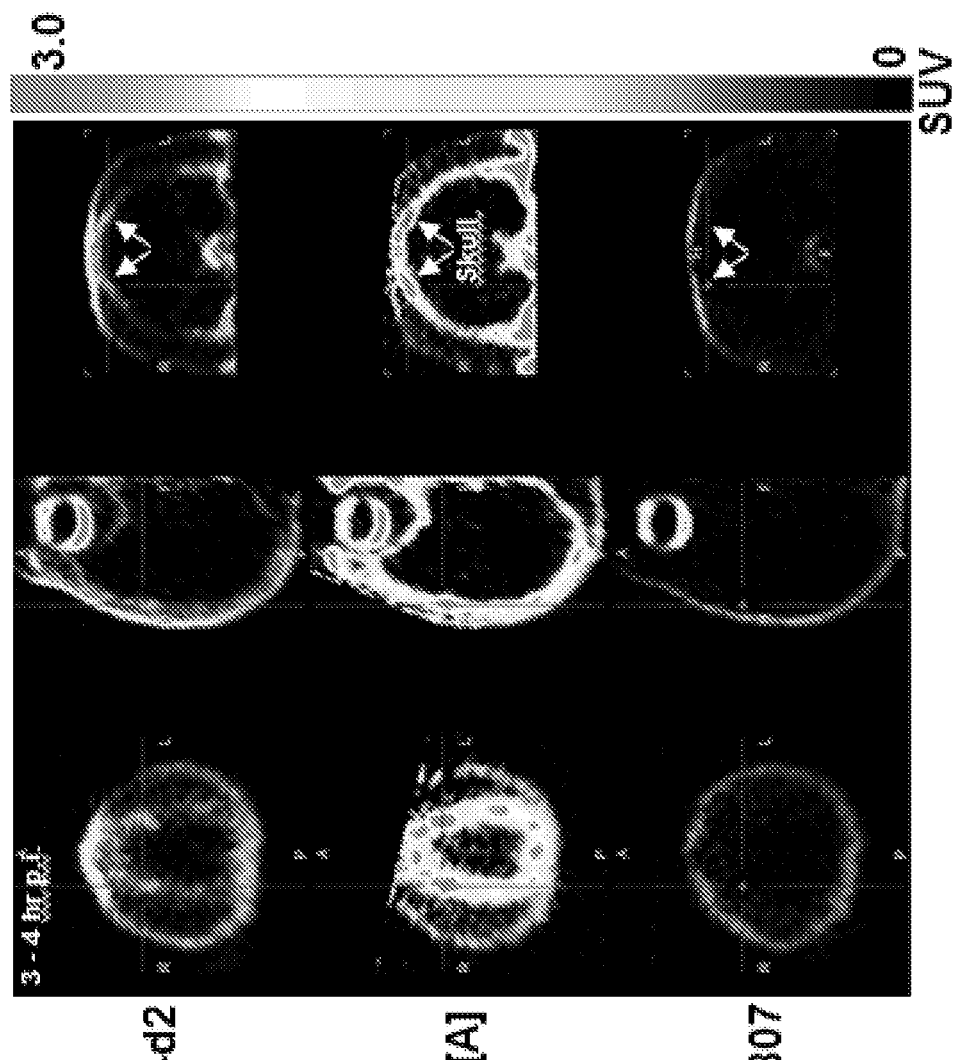
FIGS. 8A, 8B: [$^{18}$F][A]-d2, [$^{18}$F][A] or $^{18}$F T807 (370 MBq (10 mCi)) was intravenous bolus injected into an anesthetized rhesus, and dynamic PET data acquired over 240 minutes. Standard Uptake Values ([Radioactivity]/(injected dose/body weight)) were measured in the indicated structures from the reconstructed PET data. Data was collected from the same animal but on different days for each probe. [$^{18}$F][A]-d2 exhibited increased stability reflected by a reduction of skull uptake of free fluoride.
Figure 8B:
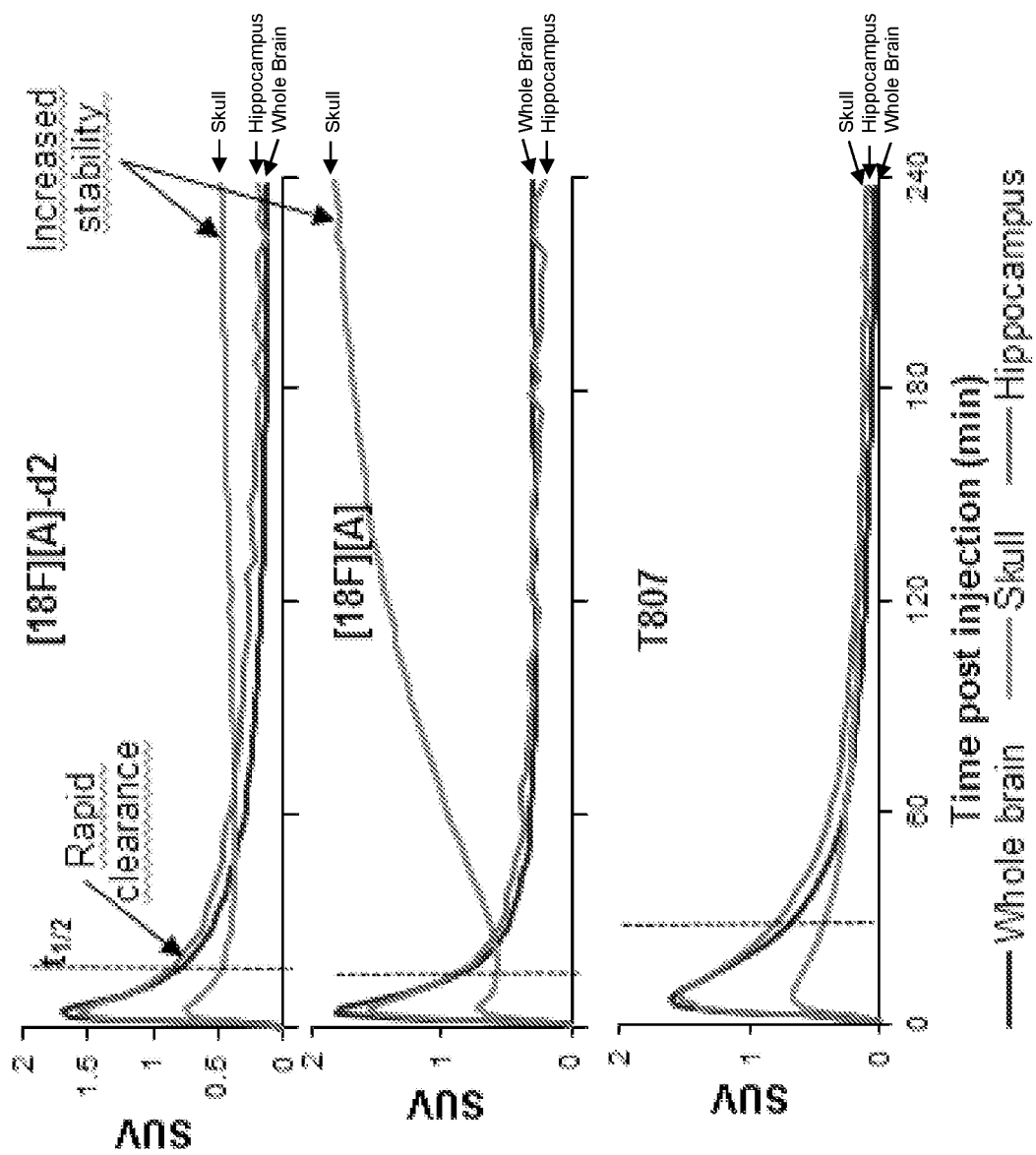

[$^{18}$F][A]-d2, [$^{18}$F][A] or $^{18}$F T807 (see Chien et al., J. Alzheimers Dis, 38:171-84 (2014)) (370 MBq (10 mCi)) was intravenous bolus injected into an anesthetized rhesus, and dynamic PET data acquired over 240 minutes. Standard Uptake Values ([Radioactivity]/(injected dose/body weight)) were measured in the indicated structures from the reconstructed PET data (as shown in FIGS. 8A, 8B). Data was collected from the same animal but on different days for each probe. [$^{18}$F][A]-d2 exhibited increased stability reflected by a reduction of skull uptake of free fluoride.

Human Administration of [$^{18}$F][A]-d2

A total of 5 subjects, 3 Alzheimer's disease (AD) patients and 2 healthy volunteers (HV) was used in this study. This study protocol required each subject to complete the following components: screening evaluation, MRI, [$^{18}$F]florbetapir (AD subjects only) and [$^{18}$F][A]-d2. The screening procedures included neuropsychological assessment, vital signs, ECG, physical exam, MRI, and [$^{18}$F]florbetapir PET imaging to confirm presence of amyloid deposition in patients clinically diagnosed with probable AD. In addition, each subject completed clinical assessments and clinical safety labs to ensure the subject was medically stable to complete the study protocol. The screening procedures occurred within 30 days prior to [$^{18}$F][A]-d2 imaging. Eligible subjects participated in a single [$^{18}$F][A]-d2 imaging session. The distribution of tau binding was assessed in each of the subject groups (AD and HV) to evaluate for binding to tau. For each AD subject, the distribution of Aβ and tau was compared. Tau binding in brain was assessed with PET using [$^{18}$F][A]-d2. Radioligand binding was compared in brains of HV subjects who should have minimal to negligible concentrations of tau compared to patients with AD, who are expected to have moderate to high densities of tau.

All subjects received a single injection of [$^{18}$F][A]-d2. Subjects received a bolus intravenous injection of no more than 370 MBq (~10 mCi). Data pertaining to 3 subjects are presented below.

Imaging Procedure

Images were acquired using a HR+ PET camera in three-dimensional mode and were reconstructed using an iterative algorithm including scatter and measured attenuation correction ($^{68}$Ge source). Dynamic images were acquired upon injection (~370 MBq). The scanning protocol consisted of 2 scanning segments in the two healthy control (HC) subjects, Subjects 1 & 2 (0-120 min and ~150-180 min) and of 3 segments in the suspected AD patient, Subject 3 (0-60 min, 93-123 min and 147-177 min).

[$^{18}$F][A]-d2 Image Analysis and Preliminary Results

The MR volumetric image, a summed image of the first 15 min after tracer administration of [$^{18}$F][A]-d2 were coregistered using Statistical Parametic Mapping SPM8 (software provided by members and collaborators of the Wellcome Trust Centre for Neuroimaging). Alignment of the additional PET segments to the first PET segment was performed using in-house developed analysis software written in Matlab® (version 8 Release 2014a). Then, using the MRI scan for anatomical delineation, irregular regions of interest (ROI) were drawn for each subject in the frontal, parietal, occipital, and temporal lobes, cerebellum gray, and white-matter (centrum semi-ovale) using MIM® software.

[$^{18}$F][A]-d2 tissue time activity curves (TAC) were expressed in SUV (Standardized Uptake Value) using each subject's weight and the corresponding tracer injected dose: TAC(SUV)=TAC(Bq/cm$^3$)×1000 cm$^3$/kg×Subject's weight (kg)/Injected dose(Bq). TAC creation and all subsequent analyses were performed using in-house developed analysis software written in Matlab®.

Figure 9:
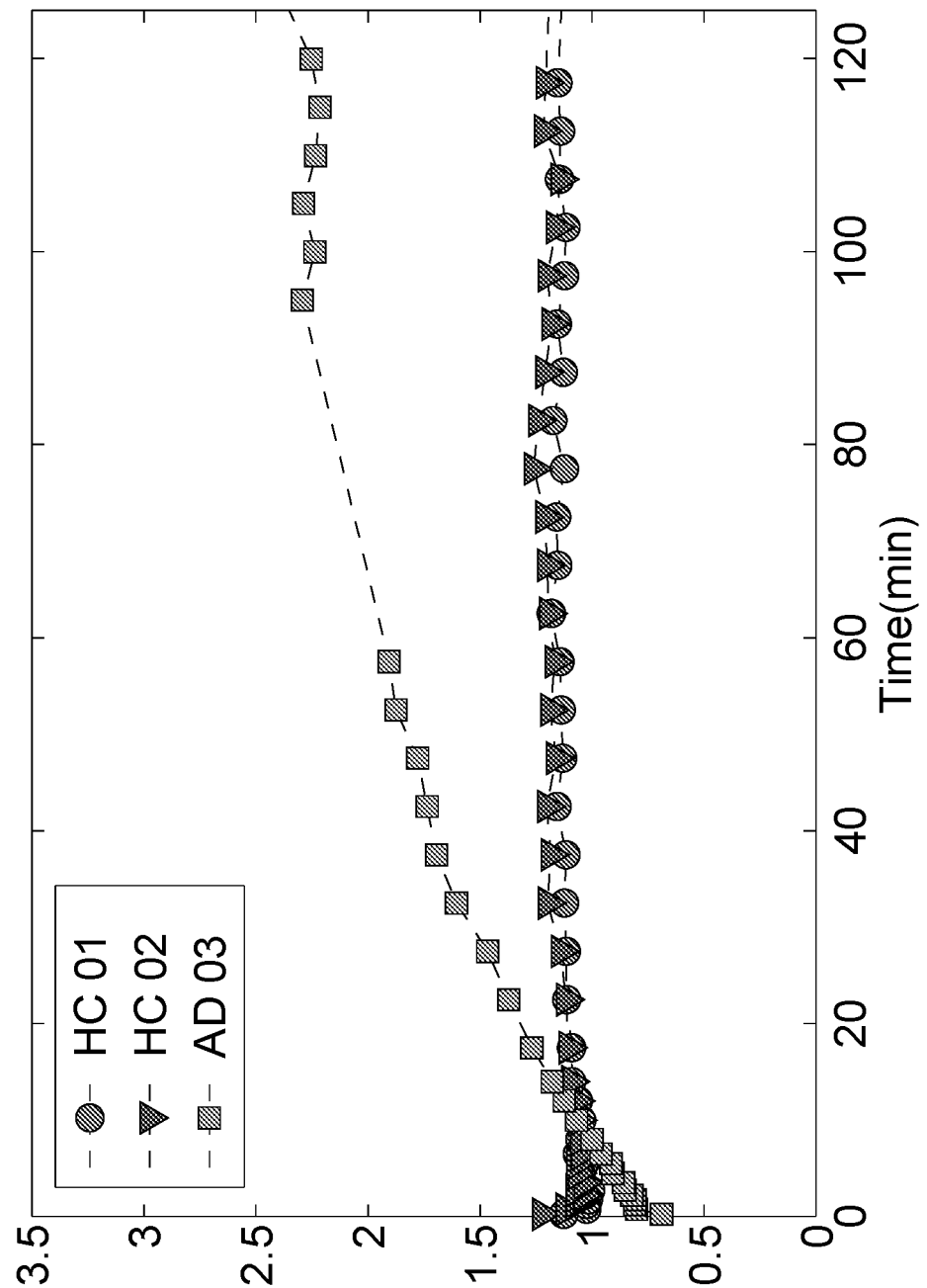
FIG. 9: The temporal lobe [$^{18}$F][A]-d2 standardized uptake value ratio (SUVR) vs. mean frame time in 3 subjects:2 healthy controls (HC) and one suspected Alzheimer's patient (AD).

The ratio to cerebellum gray or standardized uptake value ratio (SUVR) was calculated. FIG. 9 shows the temporal lobe SUVR vs. mean frame time in the 3 subjects. A clear separation of the curves is observed as early as 30 min post injection. The SUVR curves in the two healthy controls remained relatively constant soon after injection. The SUVR in the AD subject reached a plateau in the 90-120 min interval.

The average values in the 40-60 min and 90-120 min intervals following tracer injection are shown in Tables 1 and 2, respectively. SUVR values are larger in the AD subject, consistent with increased tau burden in the brain.

TABLE 1

SUVR values in the 40-60 min interval following [$^{18}$F][A]-d2 administration. Cerebellum gray as reference region

| Subject | Frontal lobe | Parietal lobe | Temporal lobe | Occipital lobe | White matter |
|---|---|---|---|---|---|
| 1 (HC) | 1.08 | 1.09 | 1.14 | 1.15 | 0.85 |
| 2 (HC) | 1.12 | 1.13 | 1.18 | 1.19 | 0.80 |
| 3 (AD) | 1.16 | 1.35 | 1.82 | 1.60 | 0.88 |

TABLE 2

SUVR values in the 90-120 min interval following [$^{18}$F][A]-d2 administration. Cerebellum gray as reference region

| Subject | Frontal lobe | Parietal lobe | Temporal lobe | Occipital lobe | White matter |
|---|---|---|---|---|---|
| 1 (HC) | 1.07 | 1.07 | 1.13 | 1.19 | 0.76 |
| 2 (HC) | 1.17 | 1.07 | 1.18 | 1.21 | 0.66 |
| 3 (AD) | 1.25 | 1.52 | 2.25 | 1.87 | 0.81 |

Figure 10:
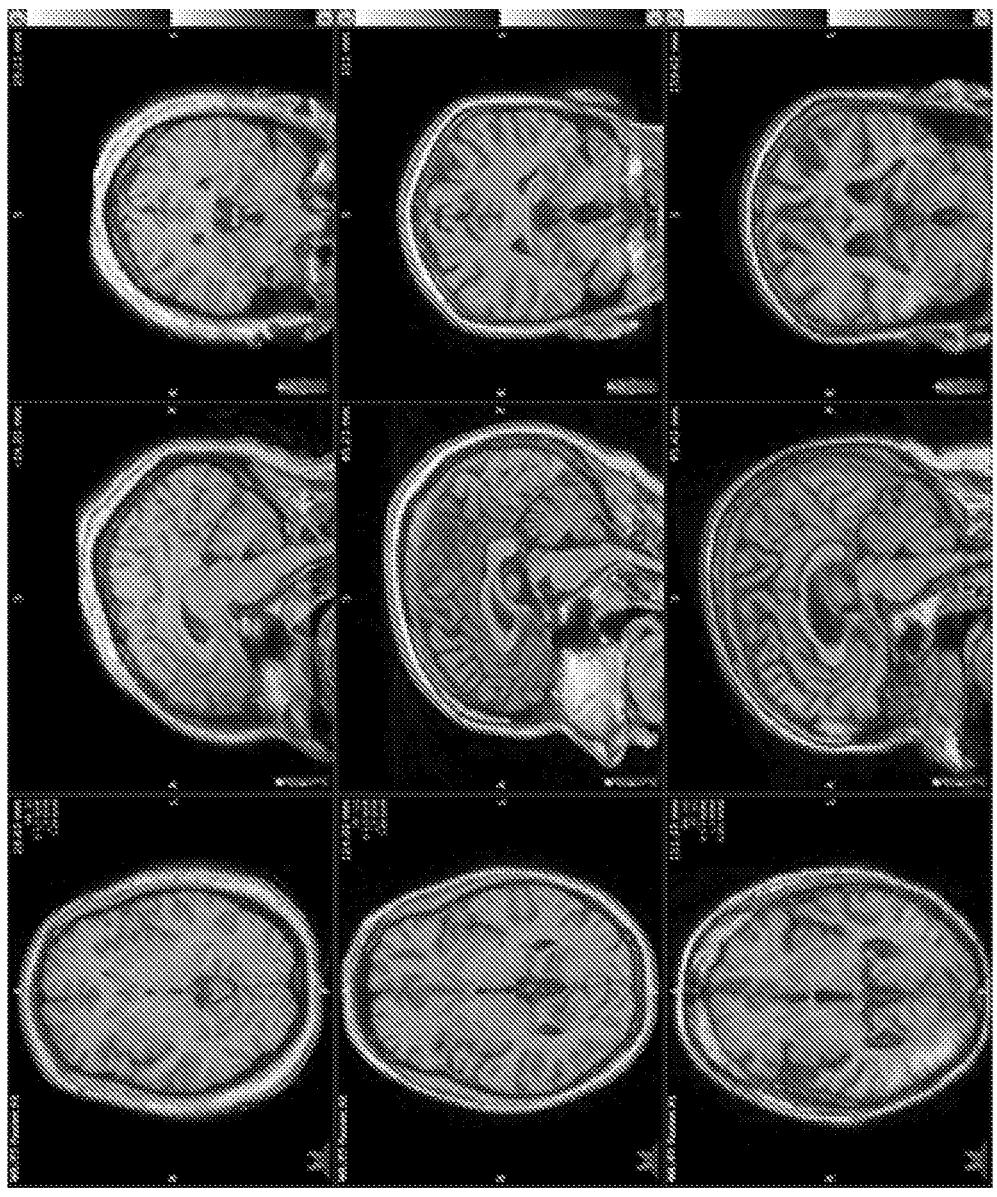
FIG. 10: Average [$^{18}$F][A]-d2 SUVR (cerebellum gray as reference) in the 90-120 min interval after tracer administration. Subjects 1-2, healthy controls (HC). Subject 3, suspected AD patient.

The images of FIG. 10 acquired in Subjects 1-3 using [$^{18}$F][A]-d2 show no radioactivity uptake in bone tissue as predicted by the in-vitro microsomal stability assay. Lack of uptake in the skull suggests negligible tracer defluorination.

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A method for detecting one or more of neurofibrillary tangles, senile plaques, or tau protein aggregation in a human subject, the method comprising:

obtaining a three-dimensional image of the subject's brain;

administering to the human subject an effective amount of a radiolabeled tracer selected from:

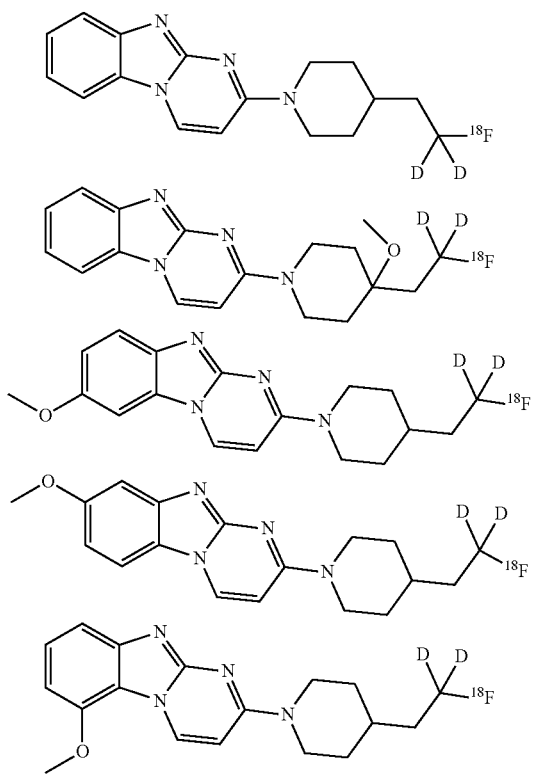

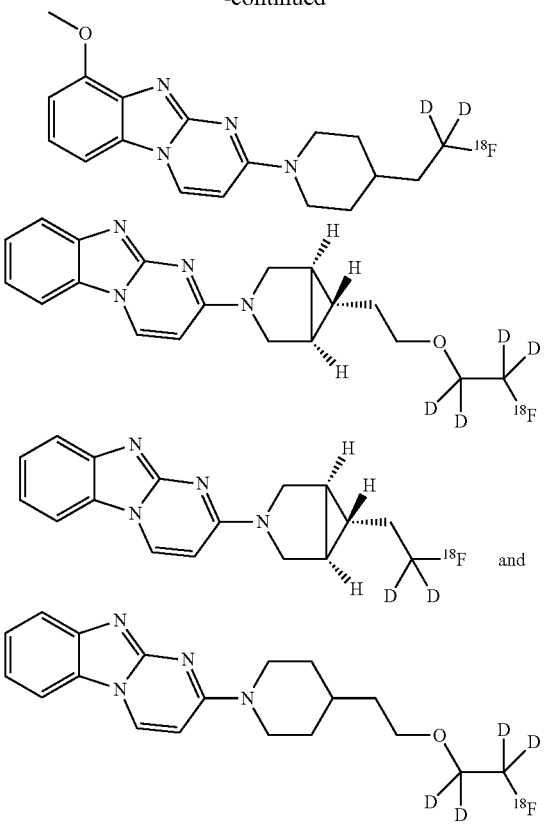

or a pharmaceutically acceptable salt thereof, wherein the effective amount is sufficient to provide an initial radiation level not greater than 370 MBq;

acquiring three-dimensional images of the subject's brain with a PET camera at one or more time intervals, thereby providing a 3D PET image of the radioactive signal of the tracer at each of the one or more time intervals;

aligning the PET images with one another and, using the MR volumetric image for anatomical delineation, identifying irregular regions of interest in the subject's brain;

measuring the standardized uptake value ratio for each region of interest relative to cerebellum gray at each of the one or more time intervals; and identifying regions having enhanced standardized uptake value ratios as containing one or more of: neurofibrillary tangles, senile plaques, or tau protein aggregation.

2. The method of claim 1 wherein the image is a MR volumetric image.

3. The method of claim 1, wherein the irregular regions are in one or more of the frontal, parietal, occipital, temporal lobes, cerebellum gray, and white matter.

4. The method of claim 1, wherein the deuterated carbon of any of the tracers has a deuterium isotopic enrichment factor of at least 3500.

5. The method of claim 1, wherein the tracer is:

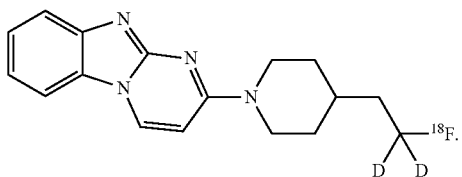

6. A method of detecting a neurological disorder, Alzheimer's disease, or progressive supranuclear palsy in a human subject, the method comprising:
obtaining a three-dimensional image of the subject's brain;
administering to the human subject an effective amount of a radiolabeled tracer selected from:

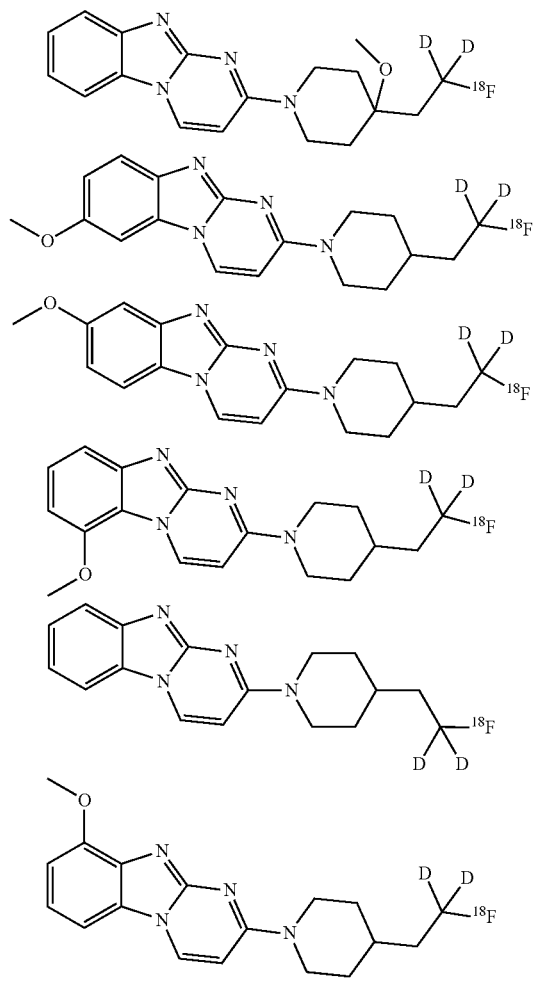

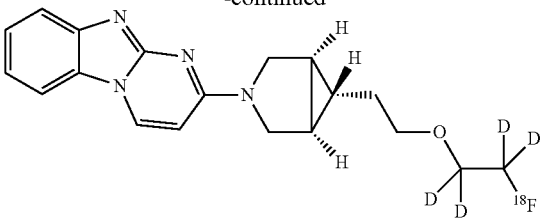

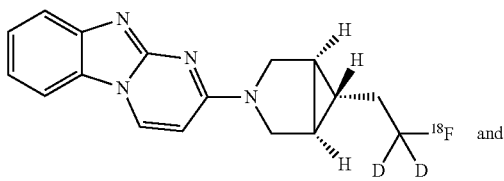

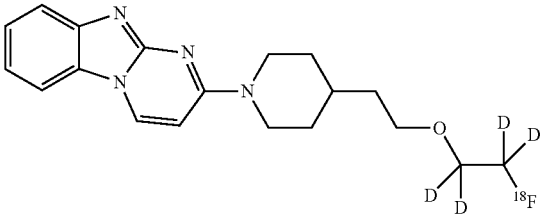

or a pharmaceutically acceptable salt thereof, wherein the effective amount is sufficient to provide an initial radiation level not greater than 370 MBq;
acquiring three-dimensional images of the subject's brain with a PET camera at one or more time intervals, thereby providing a 3D PET image of the radioactive signal of the tracer at each of the one or more time intervals;
aligning the PET images with one another and, using the MR volumetric image for anatomical delineation, identifying irregular regions of interest in the subject's brain;
measuring the standardized uptake value ratio for each region of interest relative to cerebellum gray at each of the one or more time intervals;
identifying one or more regions having enhanced standardized uptake value ratios as containing one or more of: neurofibrillary tangles, senile plaques, or tau protein aggregation; and
correlating the one or more regions having enhanced standardized uptake value ratios with onset of neurological disorder, Alzheimer's disease, or progressive supranuclear palsy in the subject.

* * * * *